US011680245B2

(12) United States Patent
Di Santo et al.

(10) Patent No.: US 11,680,245 B2
(45) Date of Patent: Jun. 20, 2023

(54) HUMAN INNATE LYMPHOID CELL PRECURSORS: IDENTIFICATION, CHARACTERIZATION, APPLICATIONS

(71) Applicants: INSTITUT PASTEUR, Paris (FR); INSTITUT NATIONAL DE LA SANTE ET DE LA RECHERCHE MEDICALE (INSERM), Paris (FR)

(72) Inventors: James Di Santo, Paris (FR); Ai Ing Lim, Paris (FR)

(73) Assignees: INSTITUT PASTEUR, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 793 days.

(21) Appl. No.: 16/463,655

(22) PCT Filed: Nov. 30, 2017

(86) PCT No.: PCT/EP2017/081041
§ 371 (c)(1),
(2) Date: May 23, 2019

(87) PCT Pub. No.: WO2018/100091
PCT Pub. Date: Jun. 7, 2018

(65) Prior Publication Data
US 2021/0108177 A1    Apr. 15, 2021

Related U.S. Application Data

(60) Provisional application No. 62/468,550, filed on Mar. 8, 2017, provisional application No. 62/428,310, filed on Nov. 30, 2016.

(51) Int. Cl.
| | |
|---|---|
| *G01N 33/53* | (2006.01) |
| *C12N 5/0789* | (2010.01) |
| *A61K 49/00* | (2006.01) |
| *G01N 33/50* | (2006.01) |
| *C12N 5/0775* | (2010.01) |
| *G01N 33/68* | (2006.01) |
| *G01N 15/14* | (2006.01) |

(52) U.S. Cl.
CPC ........ *C12N 5/0647* (2013.01); *A61K 49/0008* (2013.01); *C12N 5/0662* (2013.01); *G01N 15/14* (2013.01); *G01N 33/5047* (2013.01); *G01N 33/5094* (2013.01); *G01N 33/6869* (2013.01); *C12N 2501/2301* (2013.01); *C12N 2501/2302* (2013.01); *C12N 2501/2307* (2013.01)

(58) Field of Classification Search
None
See application file for complete search history.

(56) References Cited

U.S. PATENT DOCUMENTS 8,809,052 B2 *  8/2014  Revel ............... C12N 5/0619
                                                 435/325

FOREIGN PATENT DOCUMENTS

WO    2009/066811 A1    5/2009

OTHER PUBLICATIONS

Pearson et al (Trends in Immunology, 2012, vol. 33, No. 6, pp. 289-296). (Year: 2012).*
European Patent Office, International Search Report for PCT/EP2017/081041 dated Jan. 25, 2018 (3 pages).
Ishizuka et al., "The Innate Lymphoid Cell Precursor," Annual Review of Immunology, 34(1):299-316 (2016).
Constantinides et al., "A committed precursor to innate lymphoid cells," Nature, 508(7496):397-401 (2014).
De Grove et al., "Characterization and Quantification of Innate Lymphoid Cell Subsets in Human Lung," PLoS One, 11(1):e0145961 (2016).
Jeffery et al., "Phenotype of human intrahepatic innate lymphoid cell subsets in health and disease," Hepatology, 64(1):833A (2016).
Hazenberg and Spits. Human innate lymphoid cells. Blood, 2014, 124(5), 700-709.
Killig et al. Recognition strategies of group 3 innate lymphoid cells. Frontiers in Immunology, 2014, 5, 142, 1-8.

* cited by examiner

*Primary Examiner* — Celine X Qian
(74) *Attorney, Agent, or Firm* — Arrigo, Lee, Guttman & Mouta-Bellum LLP

(57) ABSTRACT

Innate lymphoid cells (ILCs) represent innate versions of T helper and cytotoxic T cells that differentiate from committed ILC precursors (ILCP). Still, how ILCP relate to mature tissue-resident ILCs remains unclear. ILCP that are present in the blood and all tested lymphoid and non-lymphoid human tissues were identified. Human ILCP fail to express the signature transcription factors (TF) and cytokine outputs of mature NK cells and ILCs but are epigenetically poised to do so. Human ILCP robustly generate all ILC subsets in vitro and in vivo. While human ILCP express RAR related orphan receptor C (RORC), circulating ILCP can be found in RORC-deficient patients that retain potential for EOMES$^+$ NK cells, T-BET$^+$ ILC1, GATA-3$^+$ ILC2 and for IL-22$^+$ but not for IL-17A$^+$ ILC3. A model of tissue ILC differentiation ('ILC-poiesis') is proposed whereby diverse ILC subsets are generated in situ from ILCP in response to environmental stressors, inflammation and infection.

9 Claims, 18 Drawing Sheets

Figure 1
A
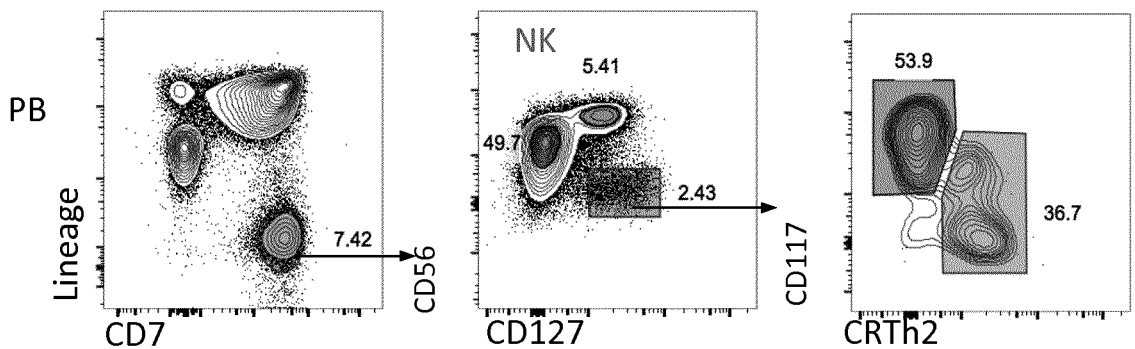
B
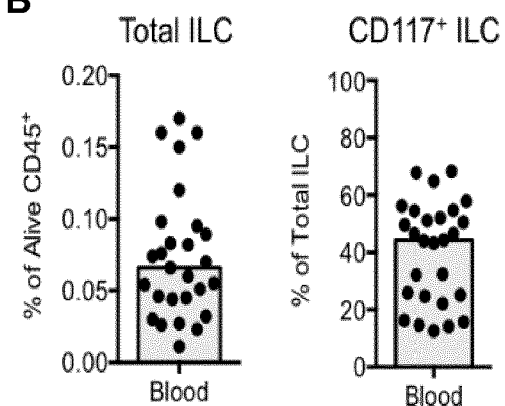
C
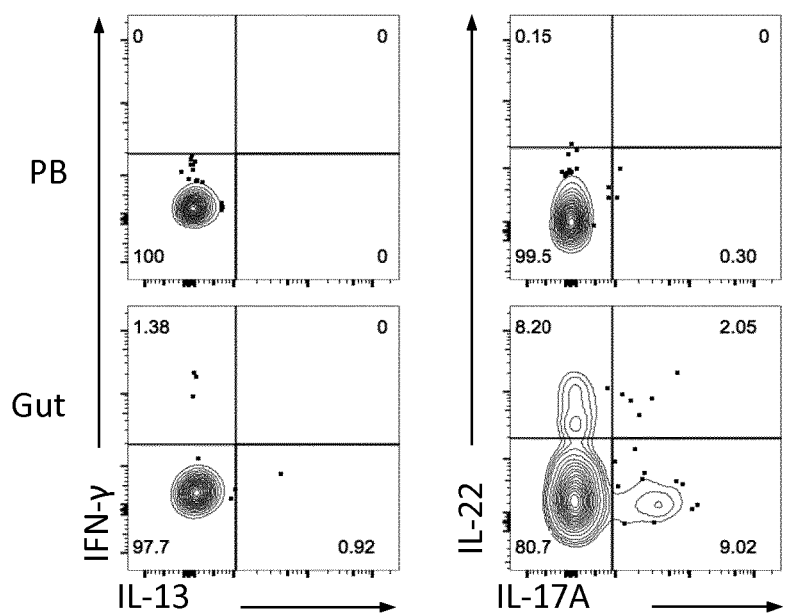

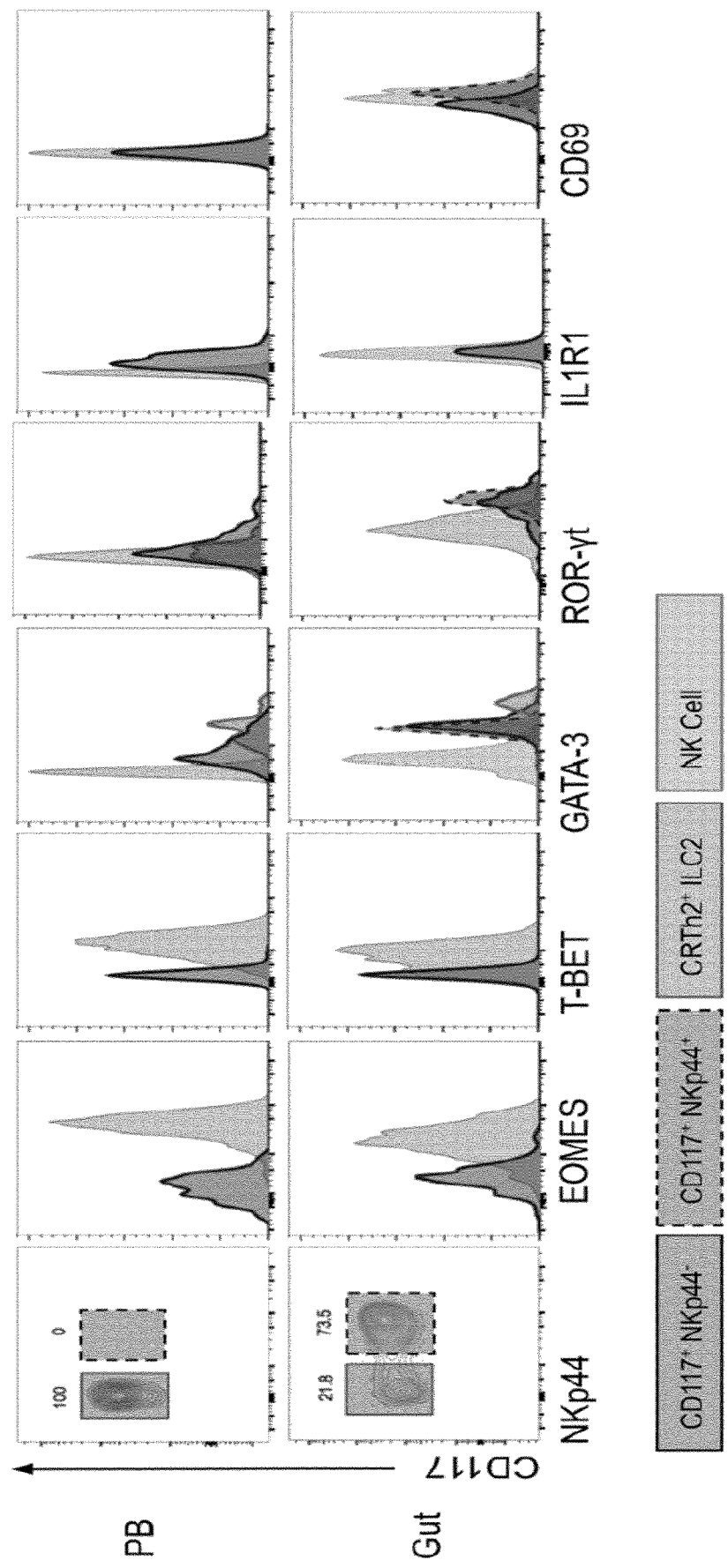

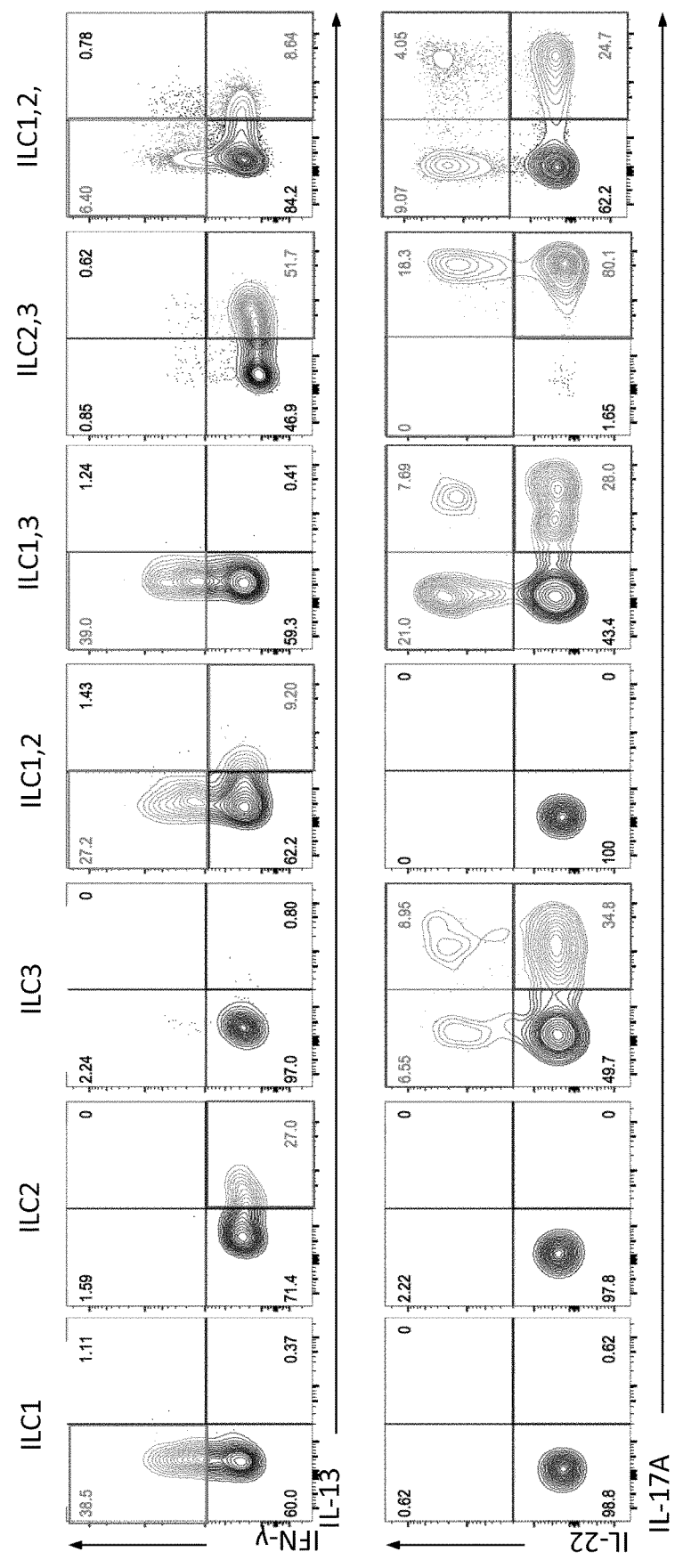

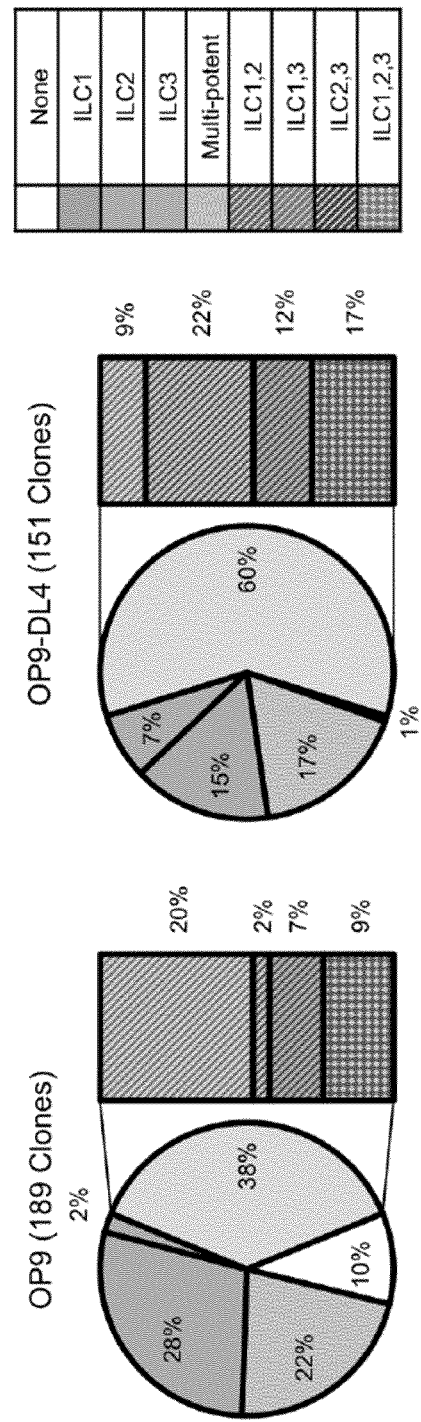

Figure 5
A
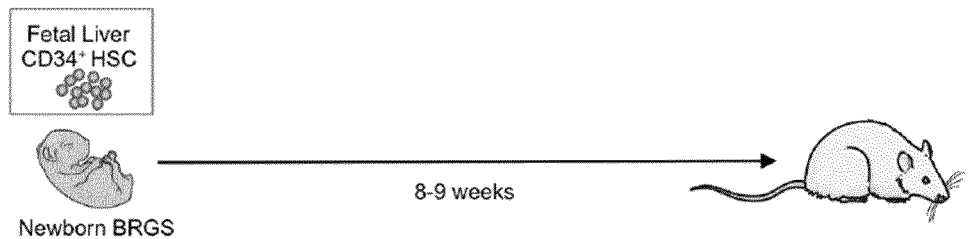
B
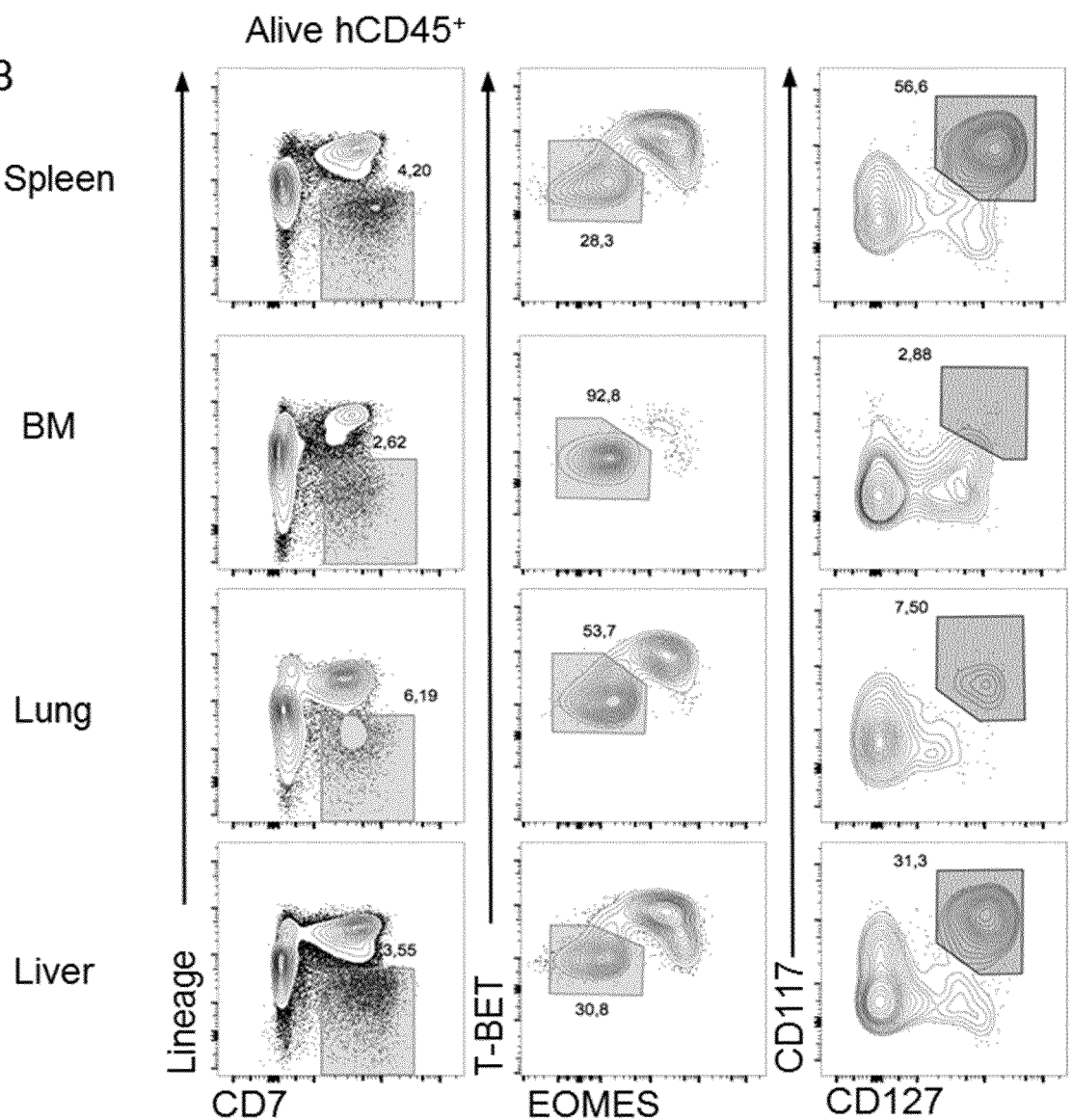

C *(continuation of figure 5)*
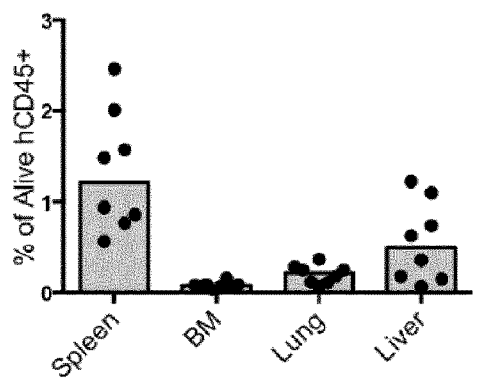
D
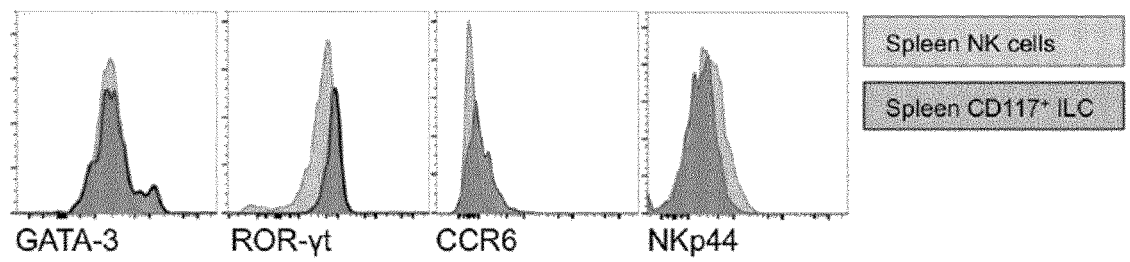
E
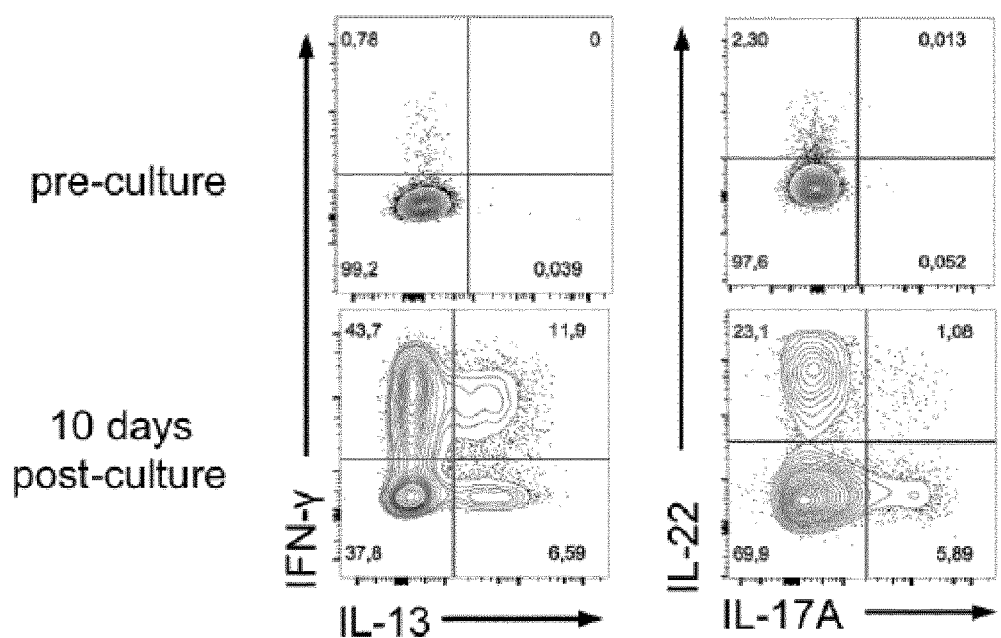

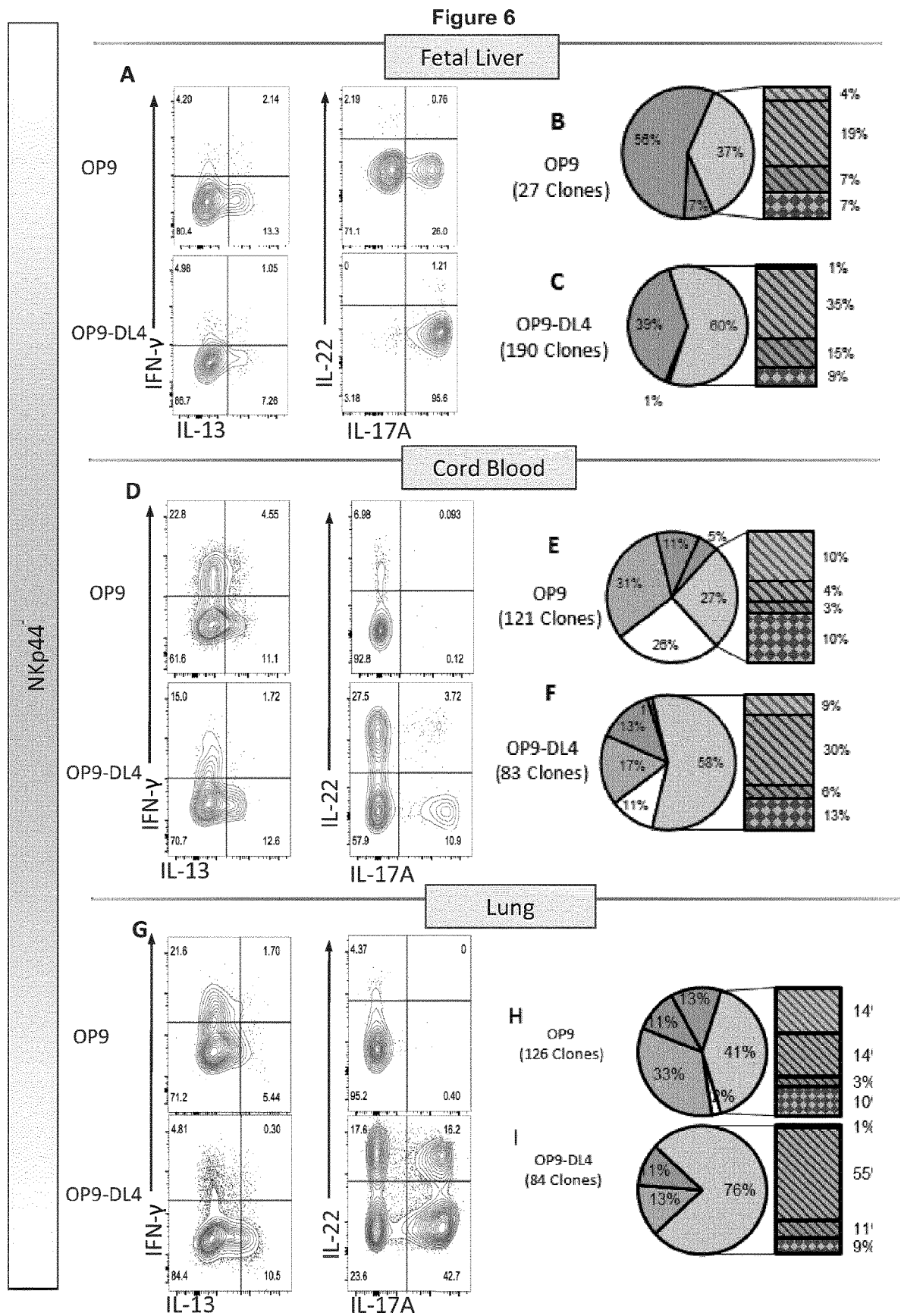

(Continuation of figure 6)
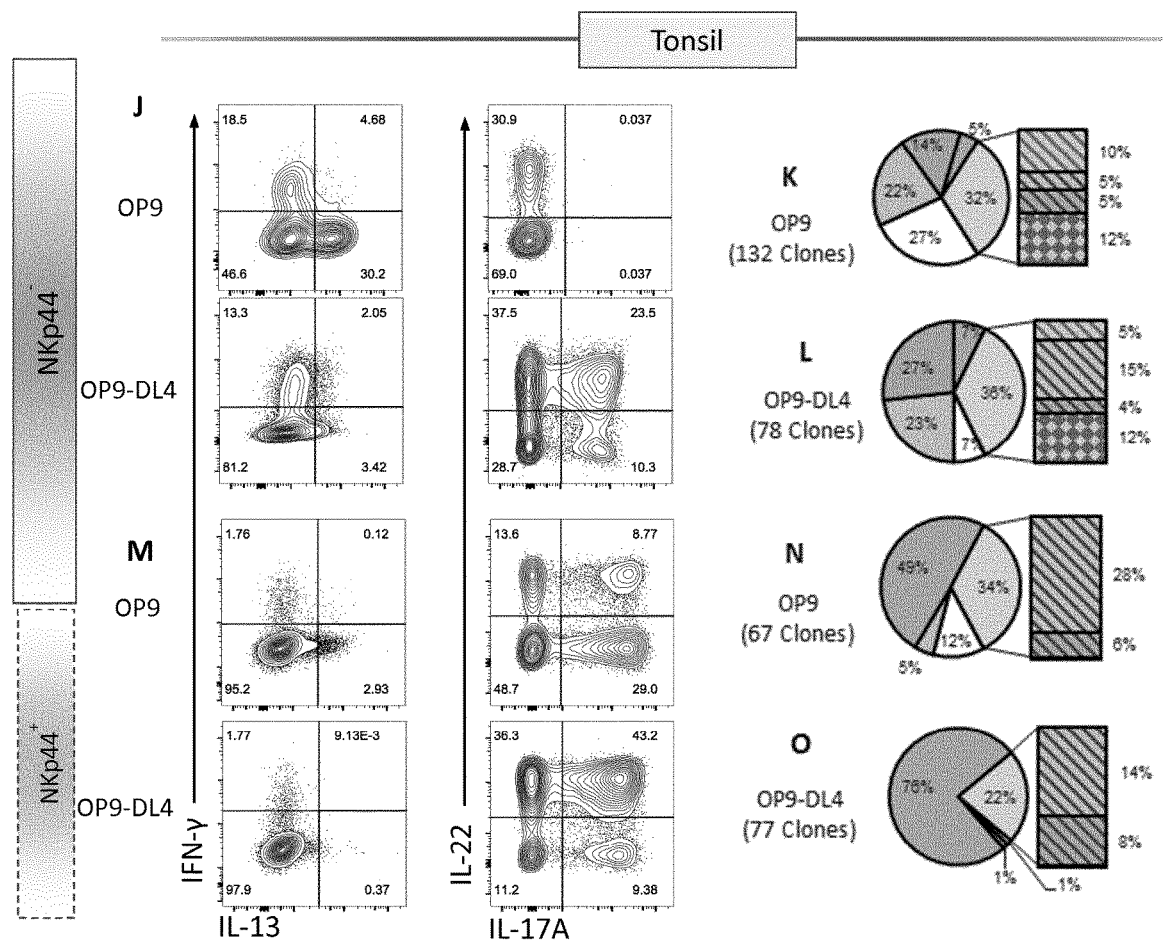

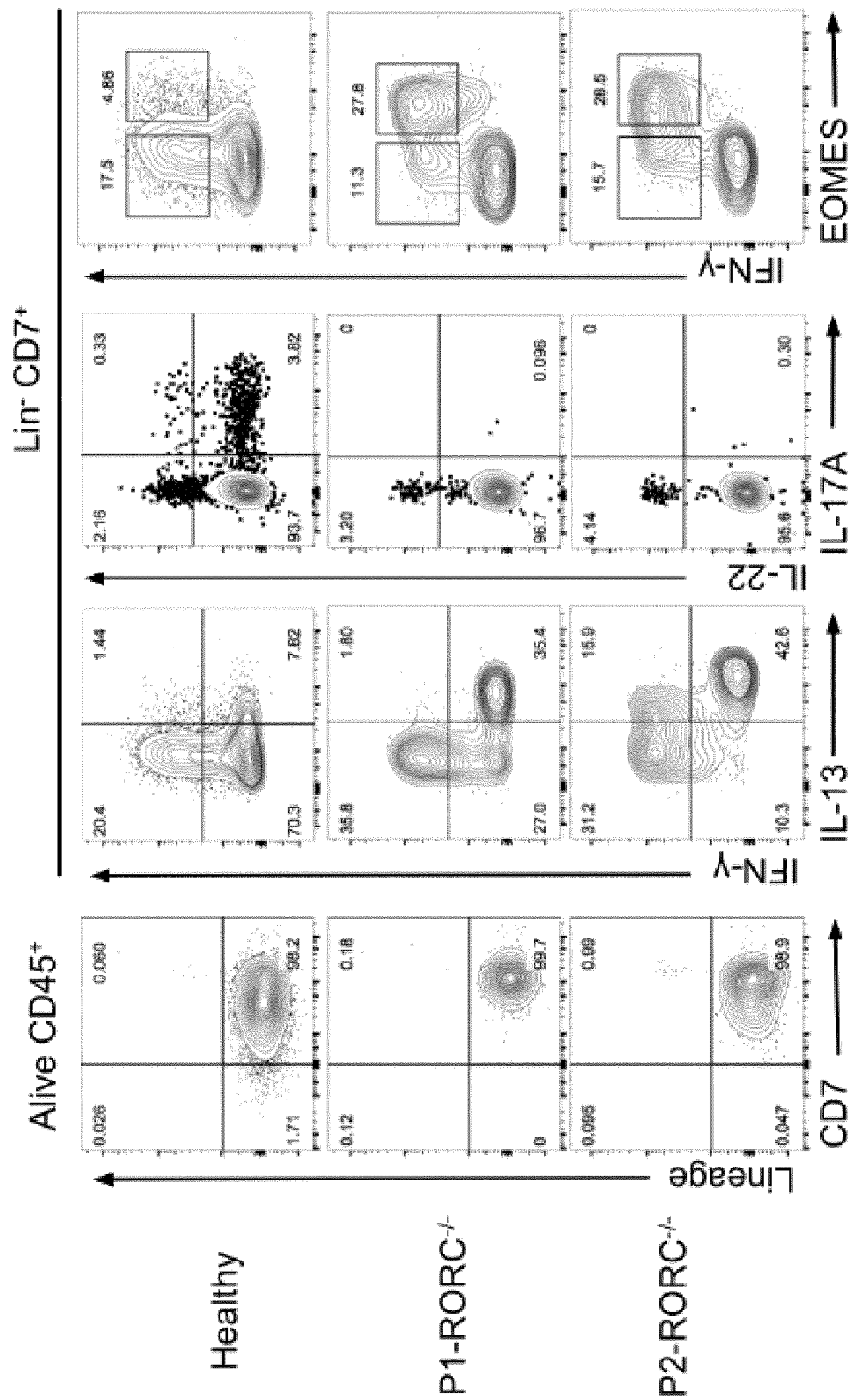

HUMAN INNATE LYMPHOID CELL PRECURSORS: IDENTIFICATION, CHARACTERIZATION, APPLICATIONS

BACKGROUND OF THE INVENTION

Innate lymphoid cells (ILC) are a novel family of lymphoid effector cells that serve essential roles in the early immune response, consisting of cytotoxic cells (NK cells) and 'helper-like' ILCs. The later are characterized by expression of interleukin-7 receptor (IL-7Rα/CD127) and categorized into three distinct groups based on their transcription factors (TF) and signature cytokines production similarities to T helper ($T_H$) cells. Group 1 ILC (ILC1) express T-BET/TBX21 and produce $T_H1$-associated cytokines IFN-γ and TNF-α. Group 2 ILC (ILC2) secrete $T_H2$-associated cytokines, IL-5 and IL-13 via a GATA-3 and RORα-dependent pathway. Group 3 ILC (ILC3) utilize related orphan receptor C (RORC encoding RORγt) to drive production of the $T_H17$-associated cytokines, IL-17 and/or IL-22 (Serafini et al., 2015; Spits et al., 2013). These different ILC subsets are found in diverse lymphoid and non-lymphoid tissues, and enriched at mucosal sites where they play essential roles in barrier function and innate immune defense (Artis and Spits, 2015; Eberl et al., 2015).

Diverse human ILC subsets were first identified in secondary lymphoid tissues and subsequently reported at several non-lymphoid tissue sites (intestine, lung, liver, skin) (reviewed in (Juelke and Romagnani, 2016)).

Group 1 ILCs can produce type 1 cytokines (e.g., IFNγ and TNF) and comprise Natural killer (NK) cells and ILC1s (Wikipedia). ILC1s are weakly cytotoxic cells closely related to ILC3s (id.). NK cells are cytotoxic innate effector cells (id.). They are distributed throughout the blood, organs, and lymphoid tissue and make up around 15% of the peripheral blood lymphocytes (id.). NK cells play a role in tumor surveillance and the rapid elimination of virus-infected cells (id.).

Two distinct populations of IFN-γ-producing ILC1 have been described. A T-BET⁺ cell expressing high levels of CD127 (referred as CD127⁺ ILC1) and CD161 but lacking other specific surface markers has been identified in tonsil and inflamed intestine (Bernink et al., 2013). In contrast, an intraepithelial ILC1 expressing NKp44 and CD103 but not CD127 resides at mucosal sites (Fuchs et al., 2013). Both these ILC1s produce IFN-γ in respond to IL-12 and can be differentiated from NK cells by minimal Eomesodermin (EOMES) expression.

Group 2 ILCs can produce type 2 cytokines (e.g. IL-4, IL-5, IL-9, IL-13) (Wikipedia). ILC2s (also termed natural helper cells, nuocytes, or innate helper 2 cells) play the crucial role of secreting type 2 cytokines in response to helminth infection (id.). They have also been implicated in the development of allergic lung inflammation (id.). They express characteristic surface markers and receptors for chemokines, which are involved in distribution of lymphoid cells to specific organ sites (id.). They require IL-7 for their development, which activates two transcription factors (both required by these cells)-RORα and GATA3. ILC2s are critical for primary responses to local Th2 antigens in the lung but are dispensable for responses to systemically delivered Th2 antigens (id.).

Human GATA-3⁺ ILC2 express the chemoattractant receptor CRTh2, IL-25R and IL-33R (Mjösberg et al., 2011), are widely distributed (Montaldo et al., 2015) (lung, skin, gut, nasal polyp, adipose tissues) and produce type 2 cytokines IL-5 and IL-13 under a variety of physio- and pathological situations (reviewed in (Kim and Artis, 2015)).

Group 3 ILCs are defined by their capacity to produce cytokines IL-17A and/or IL-22 (Wikipedia). They comprise ILC3s and lymphoid tissue-inducer (LTi) cells (id.). ILC3s are a lymphoid cell population that can produce IL-22 and expresses NKp46 (an NK cell activating receptor) (id.). Nevertheless, ILC3s differ from NK cells, as they are dependent on transcription factor RORγt, they lack cytotoxic effectors (perforin, granzymes and death receptors) and they do not produce IFNγ or TNF (id.). They are found mainly in mucosal tissues and particularly in the intestinal tract (id.).

Lymphoid tissue inducer ('LTi') cells are a subset of ILCs expressing molecules required for the development of lymphoid tissue (id.). They are essential for development of lymphoid organs during embryogenesis and after birth regulate the architecture of lymphoid tissue (id.). They have also been linked to the maintenance of T cell memory (id.).

Group 3 ILC include fetal lymphoid tissue-inducer (LTi) cells as well as adult lineage⁻ CD127⁺CD117⁺ cells that express the transcription factor RORγt and produce the cytokines IL-17A and/or IL-22 (reviewed in (Montaldo et al., 2015). ILC3 have been identified in fetal mesenteric lymph nodes and spleen (Cupedo et al., 2009) and in adult tonsils, intestine, spleen, skin, lung, endometrium and decidua. A subset of ILC3 express natural cytotoxicity receptors (NCR, including NKp30, NKp44 and NKp46) and are enriched in IL-22-producing cells (Cella et al., 2009).

Murine mature ILC differentiate from hematopoietic stem cells (HSC) via a common lymphoid progenitor (CLP) to give rise to diverse ID2⁺TCF-1⁺PLZF⁺ ILC precursors (ILCP) in fetal liver (FL) and adult bone marrow (BM) (Constantinides et al., 2014; Yang et al., 2015). Diverse TF and signaling pathways regulate this process in mice (Serafini et al., 2015); in contrast, human ILC development is less well characterized (reviewed in (Juelke and Romagnani, 2016)). NK precursors (NKP) that give rise to cytotoxic CD56⁺ NK cells have been identified in FL, BM, cord blood (CB) and adult tonsil (Renoux et al., 2015), whereas committed ILC3 precursors (ILC3P) that generate IL22-producing NCR⁺ ILC3 in vitro are found in tonsil and intestinal lamina propria but not peripheral blood (PB), thymus or BM (Montaldo et al., 2014). A recent study identified tonsillar human ILCP that expresses RORγt and can develop into mature cytotoxic and helper ILC (Scoville et al., 2016). Interestingly, these human NKP, ILC3P and ILCP were CD34⁺ and enriched in secondary lymphoid tissues but were rare or absent from the circulation. It was unclear if such ILCP were developmentally related to mature ILC subsets found in tissues.

Innate lymphoid cells are important in the development of the innate immune response, and serve an important role in protective immunity and the regulation of homeostasis and inflammation (Wikipedia). Consequently, their dysregulation can lead to immune pathology such as allergy, bronchial asthma and autoimmune disease (id.). To provide sources of ILCs, there exists a need in the art for the development of compositions and methods for isolating precursor cells of ILCs. The invention fulfills this need.

BRIEF SUMMARY OF THE INVENTION

The invention encompasses compositions comprising innate lymphoid cell precursors (ILCPs), uses of the compositions, and methods of making and using these compositions.

In various embodiments, the compositions comprise a purified population of innate lymphoid cell precursors (ILCPs), wherein at least 75%, preferably at least 90%, of the cells in the population have the phenotype CD127+ CD117+CD3−CRTh2−, and optionally have the phenotype CD7+, NKp44−, CD94−, and/or Lin−, and/or optionally CD26+, and/or CD62L+. In some embodiments, at least 75%, preferably at least 90%, of the cells in the population have the phenotype CD127+CD117+Lin−CRTh2−(wherein Lin− comprises CD3−), and optionally have the phenotype CD7+, NKp44−, and/or CD94−, and/or optionally CD26+ and/or CD62L+. Preferably, at least 90% of the cells in the population have the phenotype CD127+CD117+Lin− CRTh2−CD7+ or CD127+CD117+Lin−CRTh2−CD94−, and optionally CD26+ and/or CD62L+; more preferably at least 99% or 100% of the cells in the population have the phenotype CD127+CD117+Lin−CRTh2−CD94−, and optionally CD26+ and/or CD62L+.

In one embodiment, the invention encompasses a method for making a purified population of innate lymphoid cell precursors (ILCPs) comprising providing a human cell sample, and selecting for cells in the cell sample that have the phenotype CD127+CD117+CD3−CRTh2−, and optionally have the phenotype CD7+, NKp44−, CD94−, and/or Lin−, and/or optionally CD26+ and/or CD62L+ to provide a population of cells, wherein at least 75% of the cells in the population have the phenotype CD127+CD117+CD3− CRTh2−, and optionally have the phenotype CD7+, NKp44−, CD94−, and/or Lin, and/or optionally CD26+ and/or CD62L+.

In some embodiments, the method comprises selecting for cells in the cell sample that have the phenotype CD127+ CD117+Lin−CRTh2− (wherein Lin− comprises CD3−), and optionally have the phenotype CD7+, NKp44−, and/or CD94−, and/or optionally CD26+ and/or CD62L+. In some embodiments of the method, at least 75% of the cells in the population have the phenotype CD127+CD117+Lin− CRTh2− (wherein Lin− comprises CD3−), and optionally have the phenotype CD7+, NKp44−, and/or CD94−, and/or optionally CD26+ and/or CD62L+. Preferably, at least 90% of the cells in the population have the phenotype CD127+ CD117+Lin−CRTh2−CD7+ or CD127+CD117+Lin− CRTh2−CD94−, and optionally CD26+ and/or CD62L+; more preferably at least 99% or 100% of the cells in the population have the phenotype CD127+CD117+Lin− CRTh2−CD94−, and optionally CD26+ and/or CD62L+.

In one embodiment, the invention encompasses a method for making a cell type selected from ILC1, ILC2, ILC3, and NK cells comprising providing a population of innate lymphoid cell precursors (ILCPs), subjecting the cell population to an external stimulus, and detecting an increase in a cell type selected from ILC1. ILC2, ILC3, and NK cells.

Preferably, at least 90% of the cells in the population have the phenotype CD127+CD117+CD3−CRTh2−, and optionally have the phenotype CD7+, NKp44−, CD94−, and/or Lin−, and/or optionally CD26+ and/or CD62L+. In some embodiments of the method, at least 90% of the cells in the population have the phenotype CD127+CD117+Lin− CRTh2− (wherein Lin− comprises CD3−), and optionally have the phenotype CD7+, NKp44−, and/or CD94−, and/or optionally CD26+ and/or CD62L+. Preferably, at least 90% of the cells in the population have the phenotype CD127+ CD117+Lin−CRTh2−CD7+ or CD127+CD117+Lin− CRTh2−CD94−, and optionally CD26+ and/or CD62L+; more preferably at least 99% or 100% of the cells in the population have the phenotype CD127+CD117+Lin− CRTh2−CD94−, and optionally CD26+ and/or CD62L+.

In one embodiment, the method is performed in vivo.

In one embodiment, the invention encompasses a method for treatment of a human patient comprising administering to the patient a purified population of ILCPs, wherein at least 90% of the cells in the population have the phenotype CD127+CD117+CD3−CRTh2−, and optionally have the phenotype CD7+, NKp44−, CD94−, and/or Lin−, and/or optionally CD26+ and/or CD62L+. In some embodiments of the method, at least 90% of the cells in the population have the phenotype CD127+CD117+Lin−CRTh2− (wherein Lin− comprises CD3−), and optionally have the phenotype CD7+, NKp44−, and/or CD94−, and/or optionally CD26+ and/or CD62L+. Preferably, at least 90% of the cells in the population have the phenotype CD127+CD117+Lin−CRTh2− CD7+ or CD127+CD117+Lin−CRTh2−CD94−, and optionally CD26+ and/or CD62L+; more preferably at least 99% or 100% of the cells in the population have the phenotype CD127+CD117+Lin−CRTh2−CD94−, and optionally CD26+ and/or CD62L+.

In one embodiment, the invention encompasses a method for screening for compounds that affect the development of ILCs comprising providing a population of innate lymphoid cell precursors (ILCPs), contacting the cell population with a test compound, and detecting a change in the phenotypes of the cells in the cell population.

In one embodiment, the test compound causes a reduction in the differentiation of the ILCPs. In one embodiment, the test compound causes an increase in the differentiation of the ILCPs.

In one embodiment, the method comprises infusing a mouse with the population of innate lymphoid cell precursors (ILCPs) and administering the test compound to the mouse.

In various embodiments, the cells expand without plasticity.

In one embodiment, the invention encompasses a method for expanding ILCPs, comprising culturing the purified population of ILCPs according to the invention in a culture medium comprises IL-1ß and IL-2.

In various embodiments, ILCPs are cultured in a culture medium comprises IL-1ß and IL-2.

In one embodiment, the invention encompasses a method for expanding ILC3 cells with minimal plasticity, wherein the culture medium comprises IL-1ß, IL-2 and IL-7.

BRIEF DESCRIPTION OF THE DRAWINGS

FIG. 1A-D depict characterization of peripheral blood CD117+ILC. (A) Gating strategy for FACS analysis of human PB ILC. Total ILC were gated on viable $CD45^+$ Lin−($CD3^-$ $CD4^-$ $CD5^-$ $TCR\alpha\beta^-$ $TCR\gamma\delta^-$ $CD14^-$ $CD19^-$) $CD7^+$ $CD127^+$ cells (red). NK cells are identified by $CD56^{Dim}$ (grey), ILC2 are marked by $CRTh2^+$ cells (green) and $CD117^+$ ILC are gated on $CRTh2^-$ $CD117^+$ population (blue). (B) Percentage of total ILC from viable $CD45^+$ and $CD117^+$ ILC from total ILC of healthy adult donors in PB. Results from 27 healthy individuals (Median). (C) Expression of surface phenotypes (NKp44, IL1R1 and CD69) and intracellular transcription factor (EOMES, T-BET, GATA-3 and RORγt) profiles of PB $CD117^+$ ILC and gut $CD117^+$ $NKp44^{+/-}$ ILC. (D) Functional profiles (IFN-γ, IL-13, IL-22 and IL-17A) of PB $CD117^+$ ILC and gut $CD117^+NKp44^{+/-}$ ILC in response to 3 h PMA/iono stimulation. Data representative of at least 3 individuals analyzed from at least 3 independent experiments.

FIG. 5A-E depict that human ILCP accumulate in human immune system (HIS) mice. (A) Schematic diagram of generation of HIS mice. 1.5-2×10$^5$ CD117$^+$ ILC or CD34$^+$ CD38$^-$ HSC isolated from human fetal liver were intrahepatic transferred into newborn BRGS mice. Mice were analyzed 8 to 9 weeks post-transplantation. (B) Representative FACS analysis of human ILCP (Lin$^-$ CD7$^+$ CD127$^+$ CD117$^+$) in spleen, BM, lung and liver of HIS mice. (C) Percentage of ILCP from total human CD45$^+$ in spleen, BM, lung and liver of HIS mice. (Median). (D) FACS analysis of surface phenotypes and transcription factors profiles of ILCP and NK cells from spleen of HIS mice. (E) Cytokines production of spleen CD117$^+$ ILC from HIS mice pre-culture and post-culture on OP9-DL4 with IL-2, -7, -1β, and -23 for 10 days. Cytokines production was analyzed after 3 h of PMA/iono stimulation. Representative data of 8 mice from at least 3 independent experiments.

FIG. 6A-N depict that in vitro bulk and clonal assay of CD117$^+$ ILC from lymphoid and non-lymphoid organs. Bulk (100-300 cells) or single CD117$^+$ NKp44$^{+/-}$ CD117$^+$ ILC from different organs were FACS sorted into 96-well round bottom plate pre-seeded with OP9 or OP9-DL4 and supplied with IL-2, -7, -1β and -23 (20 ng/ml each). Intracellular FACS analysis for cytokines production in respond to 3 h PMA/iono stimulation was performed to identify ILC1 (IFN-γ$^+$), ILC2 (IL-13$^+$) and ILC3 (IL-22$^+$ and/or IL-17A$^+$) after 8-10 days bulk culture (A, D, G, J, M) or 14-18 days single cell culture (B-C, E-F, H-I, K-L, N-O). Representative FACS analysis of progeny from bulk CD117$^+$ NKp44$^-$ ILC isolated from (A) FL, (D) CB, (G) lung, (J) tonsil and CD117$^+$ NKp44$^+$ from (M) tonsil. Pie chart depicting all possible ILC combinations after clonal expansion of CD117$^+$ NKp44$^-$ ILC from (B-C) FL, (E-F) CB, (H-I) lung, (K-L) tonsil and (M-N) CD117$^+$ NKp44$^+$ from tonsil on OP9 and OP9-DL4. See also FIG. 3 legend. Data summarized from at least 2 independent experiments with one donor each.

FACS analysis of cells from several normal healthy donors was performed using various markers and the percentages of the indicated cells were determined.

Figure 9:
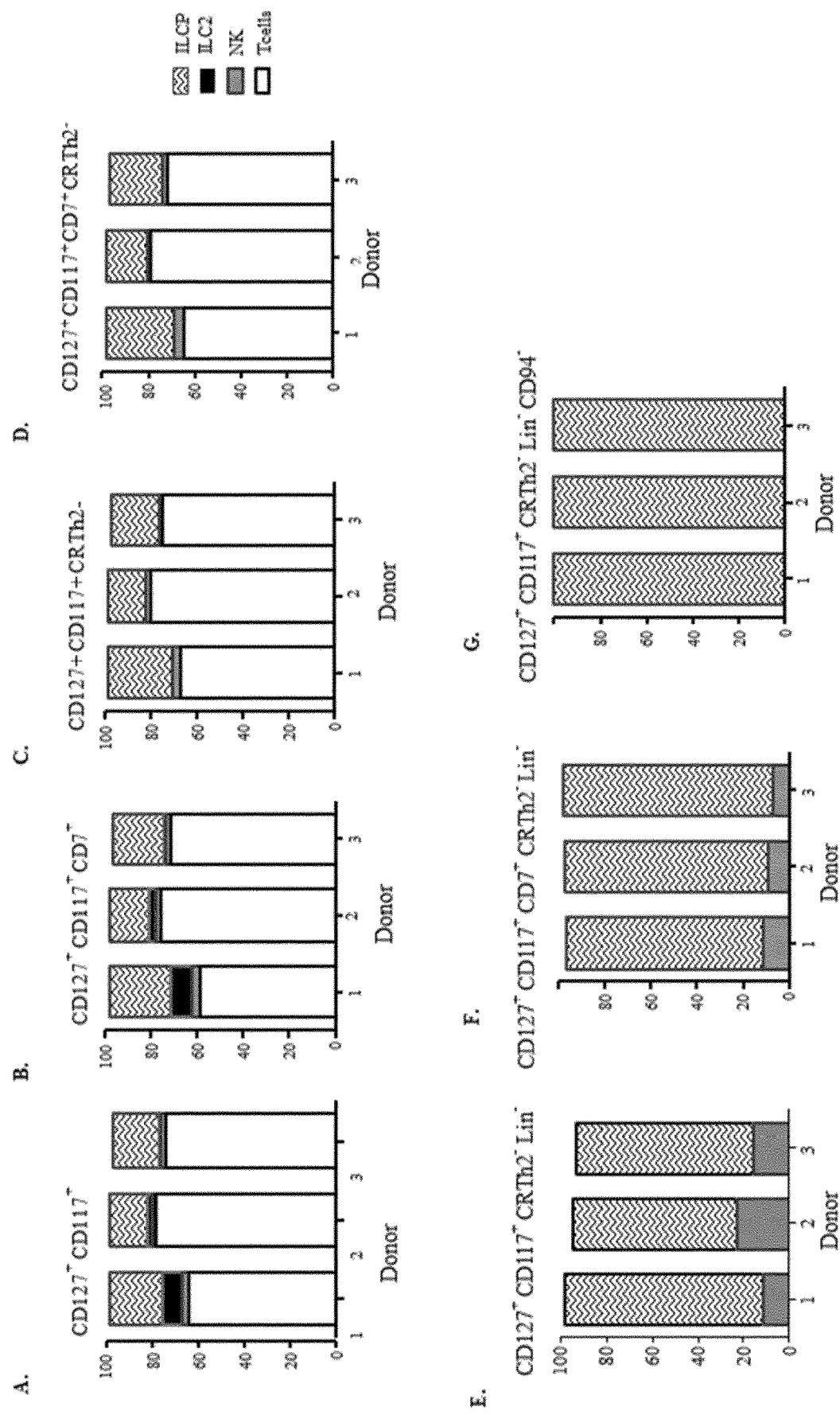

FIG. 9 A-G depict flow cytometric analysis of ILCP markers.

FACS analysis of cells from several normal healthy donors was performed using various markers and the percentages of the indicated cells were determined.

Figure 10:
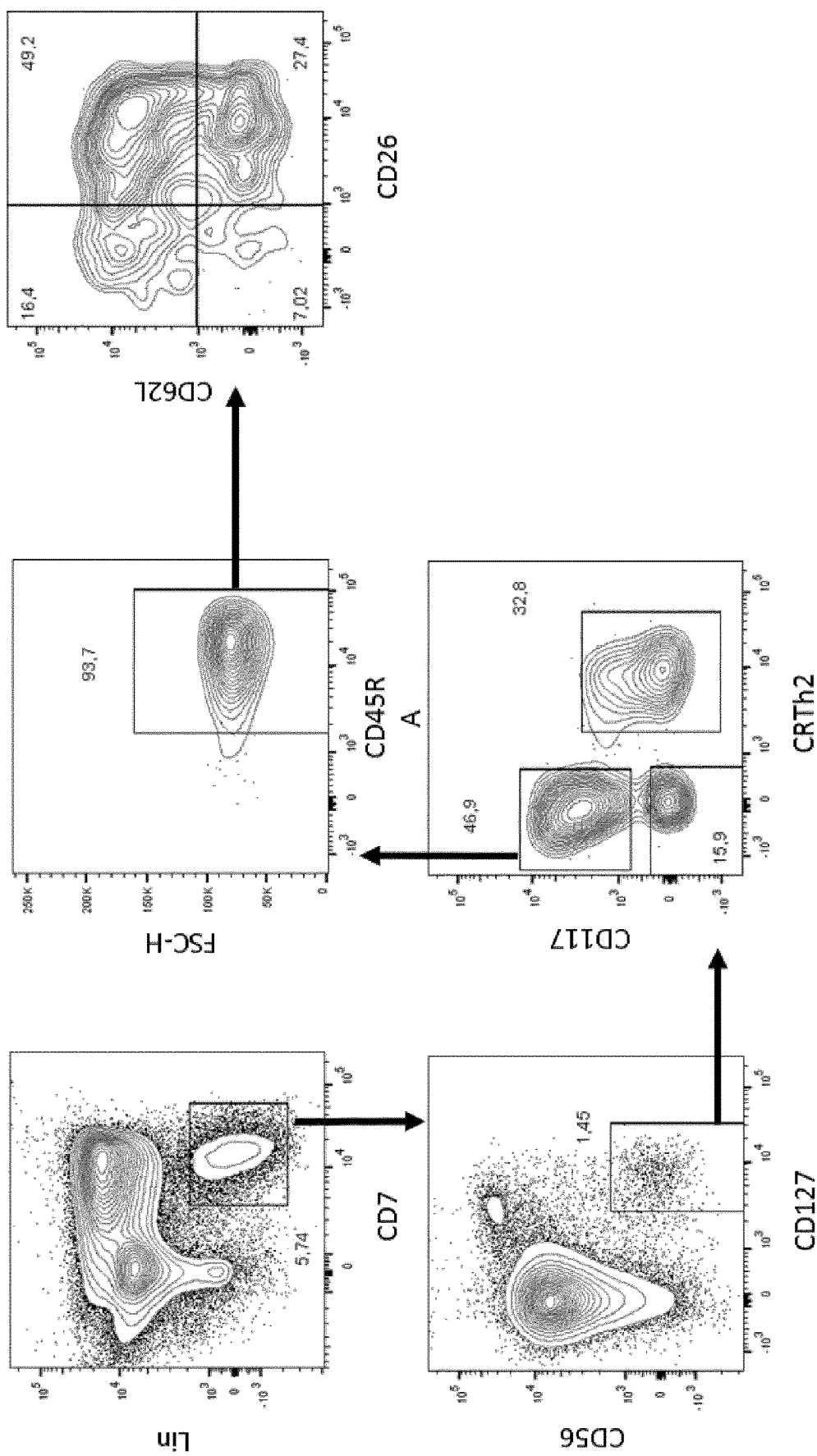

FIG. 10 depicts analysis of CD62L and CD26 human ILCP subsets.

Gating strategy for FACS analysis of lineage depleted human peripheral blood cells is shown. Within the Lin–CD7+CD127+CD117+ gate (human ILCP) there is homogeneous expression of CD45RA and variable expression of CD62L and CD26.

Figure 11:
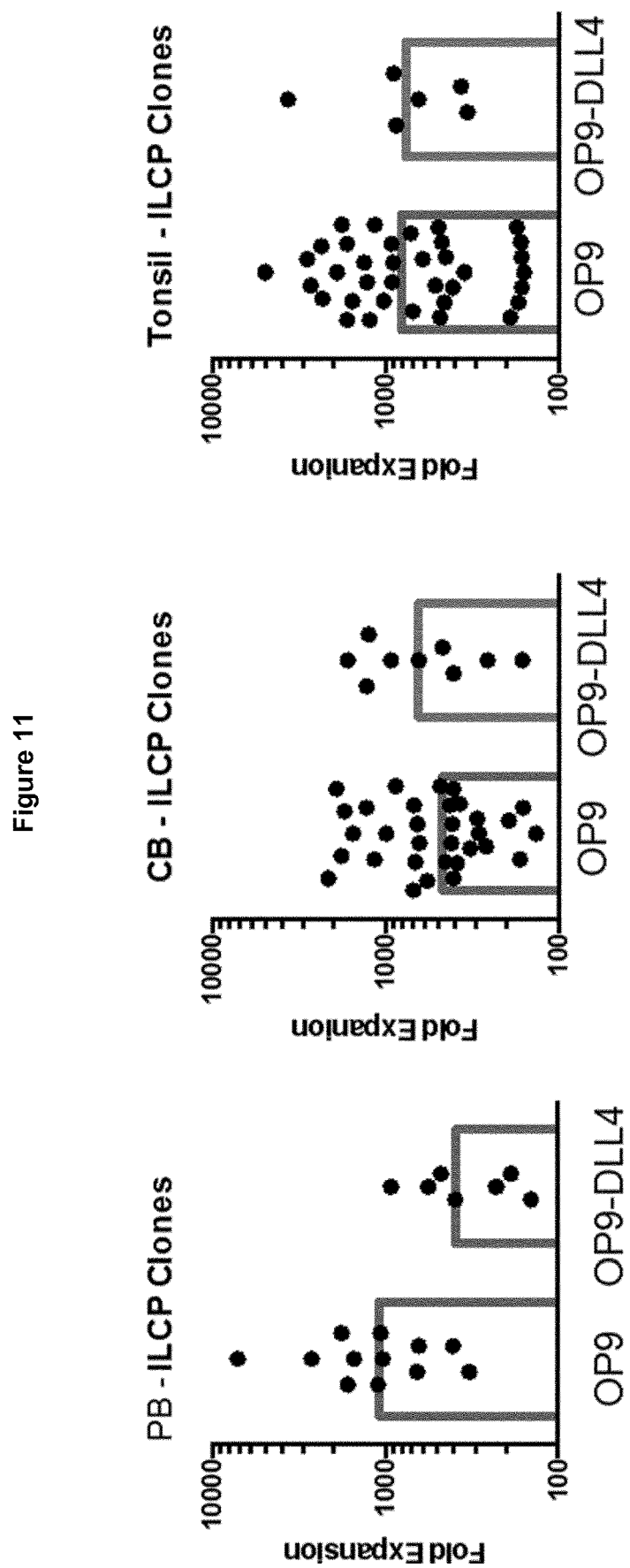

FIG. 11 depicts human ILCP clonal expansion.

Human ILCP (Lin–CD7+CD127+CD117+) were cloned from indicated tissues after single cell sorting using OP9 stromal cells (expressing or not DLL4) supplemented with human IL-1b, IL-2, IL-7 and IL-23. Clones were then analyzed for cytokine production (IFN-γ, IL-13, IL-17A, IL-22) after 3 hr stimulation with PMA/ionomycin. Putative ILCP were identified as cytokine non-producers. Absolute numbers of cells in individual ILCP clones are shown.

Figure 12:
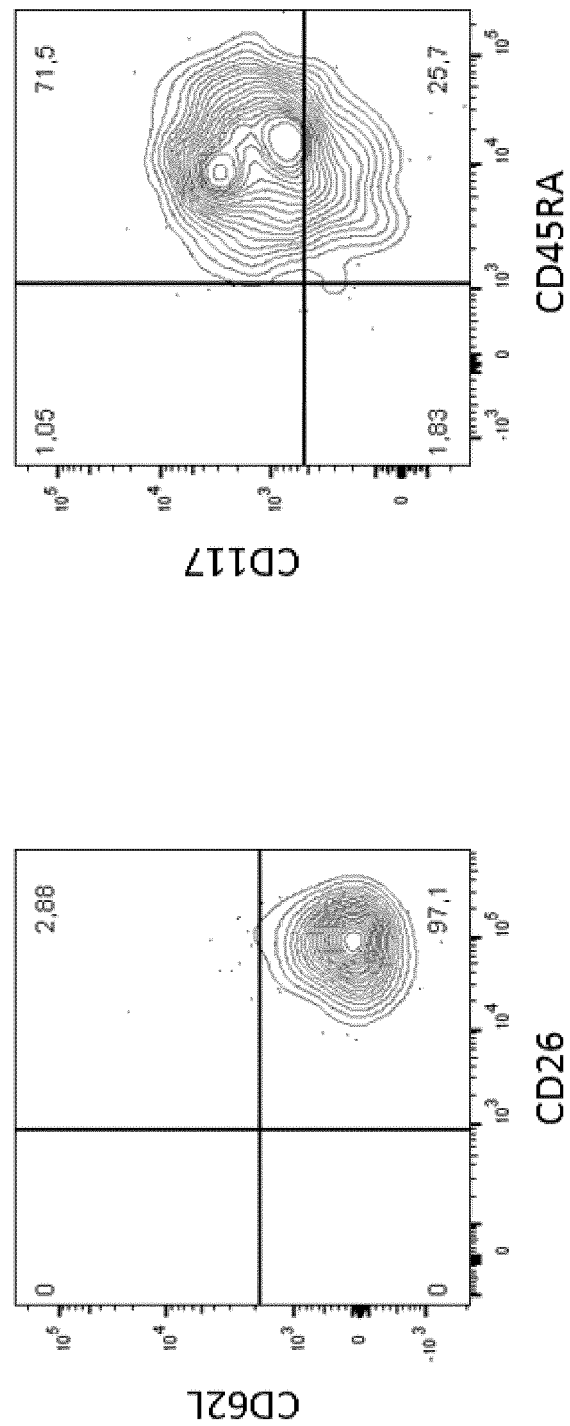

FIG. 12 depicts human ILCP clone phenotype. Human ILCP clone derived from adult peripheral blood was stained for the indicated cell surface markers.

DETAILED DESCRIPTION OF THE INVENTION

The inventors have characterized the phenotypic, molecular, and functional attributes of peripheral blood $CD117^+$ ILCs. While cells with this phenotype were previously proposed to represent human ILC3 (Hazenberg and Spits, 2014), it has been unexpectedly discovered that these cells are remarkably enriched in multi-potent and uni-potent ILC precursors (ILCP) that can give rise in vitro and in vivo to all known ILC subsets, including $EOMES^+$ NK cells. $CD117^+$ ILCP are found not only in the circulation, but also in tissues where they retain ILC multipotency. The identification of systemically distributed ILCP suggests a model whereby circulating ILCP provide a cellular substrate for ILC differentiation in tissues in response to infection, inflammation, and cell transformation.

In this report, the inventors identify and characterize human ILC precursors (ILCP) as a subset of $Lin^-CD7^+CD127^+CD117^+$ cells in cord and adult blood as well as fetal liver and several adult tissues. Human ILCP give rise to all mature ILC subsets that are capable of producing a range of cytokines (IFN-γ, IL-13, IL-17A, IL-22) after in vitro culture or after transfer in vivo to immunodeficient mice. Human ILCP also generate $EOMES^+$ NK cells demonstrating their potential for both cytokine-producing as well as cytotoxic ILCs. This is the first evidence for a circulating ILCP in any species and further demonstrate the broad systemic distribution of ILCP within human lymphoid and non-lymphoid tissues including mucosal sites.

Figure 8:
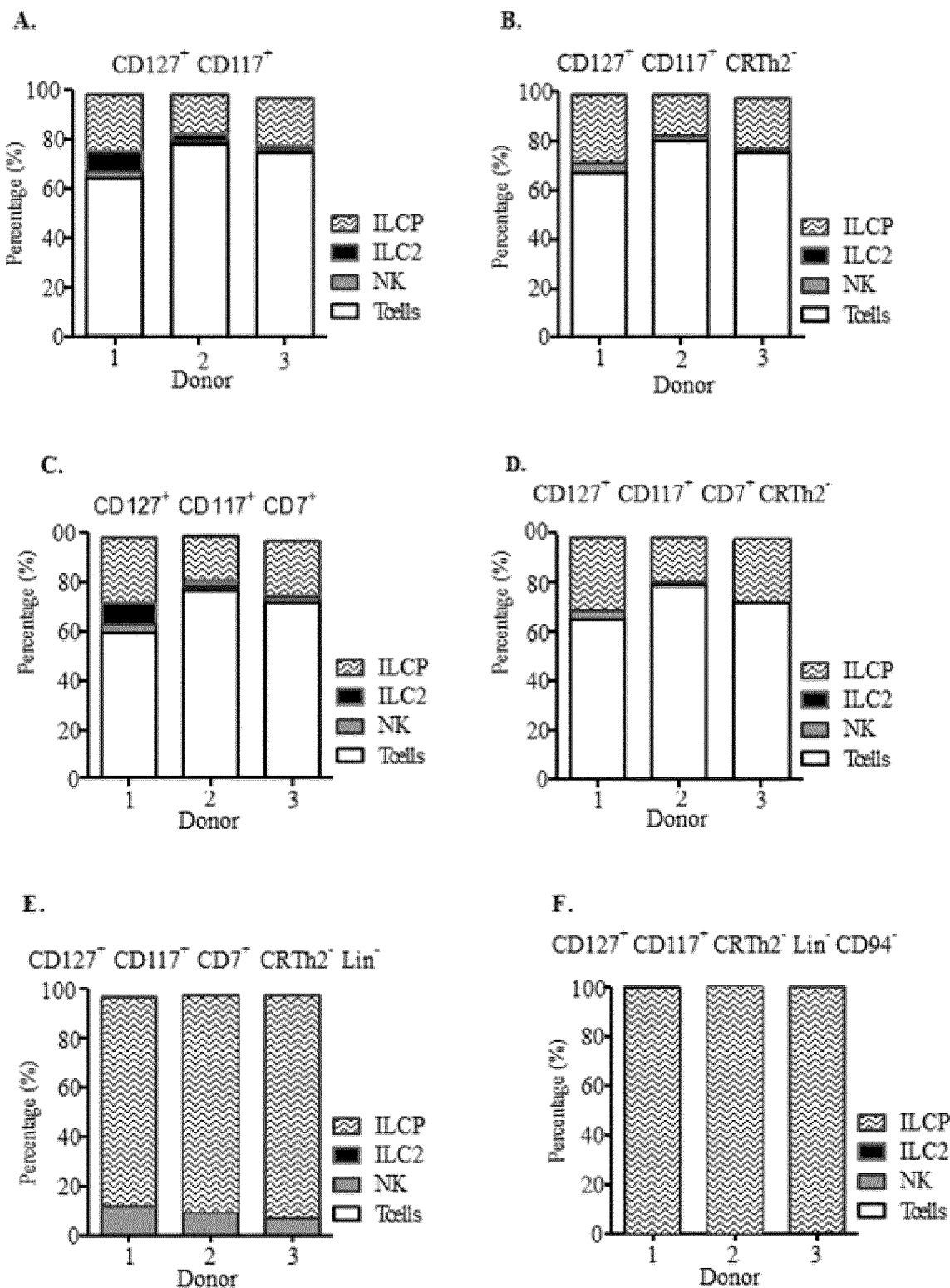
FIG. 8 A-F depict flow cytometric analysis of ILCP markers.

Sorting using the markers CD127+CD117+ cells generated about 20% ILCP and 60-80% T cells which are CD3+ (FIG. 8A or 9A). Excluding Lineage cells (including CD3) strongly enriched ILCP in CD127+CD117+ cells (FIG. 8E-F; FIG. 9E-G). Exclusion of CRTh2 ILC2 in Lin−CD127+CD117+ cells provided further ILCP enrichment, generating at least 75% of ILCP (FIG. 8E-F; FIGS. 9E, 9F and 9G). Sorting using the markers CD127+CD117+CD7+CRTh2–Lin– generated approximately 90% ILCP (FIGS. 8E and 9F). By excluding CD56+ NK cells (that are the only Lin– cells that express CD94), a pure population of ILCP could be identified. Accordingly, sorting using the markers CD127+CD117+CRTh2–Lin–CD94– generated approximately 100% ILCP (FIGS. 8F and 9G) Within the Lin+ cells, CD3+ T cells are essentially the only cells that express CD127 or CD117. As such, there is essentially no difference in the percentage of ILCP obtained when comparing CD127+CD117+CRTh2–CD3– versus CD127+CD117+CRTh2–Lin–.

The identification of human ILCP was possible thanks to a robust OP9 stromal cell-based assay that could assess ILC potential at the single cell level. Using this approach, the inventors identified uni-potent ILCP that could give rise to IFN-γ ILC1, IL-13$^+$ ILC2 or IL-17A$^+$ and/or IL-22$^+$ ILC3 as well as multi-potent human ILCP that could generate two or more ILC subsets. The inventors demonstrate that human $CD34^+$ HSC could develop in vivo into CD117 cells that harbored ILCP with multi-lineage ILC potential. Taken together, the inventors would propose a model for human ILCP development whereby pluripotent $CD34^+$ HSC would progressively differentiate into multi-potent ILCP (with the $CD34^-CD7^+CD127^+CD117^+CD45RA^+$ phenotype) that can give rise to the three main ILC groups (including $EOMES^+$ NK cells). Both $CD34^+$ HSC and multi-potent ILCP are present in fetal liver suggesting that this tissue is permissive for this transition. It will be interesting to know if the $CD117^+$ ILCP are present in human BM. Previously described human tonsillar ILCP (Scoville et al., 2016) may represent an intermediate in this pathway. The absence of $CD34^+CD117^+CD45RA^+$ ILCP in BM, as well as adult and cord blood (Scoville et al., 2016) suggests that these ILCP arise locally. The circulating and tissue-resident human ILCP that the inventors describe herein also harbor cells with more restricted uni-potent ILC. While the inventors have not identified a marker that allows distinction between multi-potent and uni-potent ILCP, the inventors assume that they retain a precursor-product relationship.

Transcriptomic and epigenomic analysis of circulating human ILCP revealed a signature consistent with a partial specification to the ILC lineage. TFs known to be critical for ILC development in mice (including TCF7, TOX, ID2 and GATA3; (Klose et al., 2014; Seehus et al., 2015; Yagi et al., 2014; Yang et al., 2015)) were clearly up-regulated in ILCP compared to circulating HSC. In contrast, signatures of early B and T lymphopoiesis were not obvious, consistent with the inability of these cells to adaptive lymphocytes in vitro or in vivo. ILC group-defining TFs (BCL2, TBX21, EOMES, RORC) were either absent or expressed at low levels suggesting commitment to ILC1, ILC2 or ILC3 was not yet completed. Interestingly, the loci encoding these factors were still 'poised' as evidenced by abundant H3K4Me2 modifications. This chromatin landscape likely facilitates rapid generation of differentiated ILC subsets following cytokine-driven expansion (Zook et al., 2016) and contrasts with the situation in naïve T cells where signature cytokine and TF loci remain inactive with dominant H3K27 methylation (Koues et al., 2016; Shih et al., 2016).

While uni-potent and multi-potent ILCP were identified in every human tissue sample tested, there were clearly differences in the relative proportions of ILCP that were uni- or multi-potent. It is therefore likely that each tissue harbors a unique ILCP 'repertoire' conditioned by environmental signals. These may include the same growth factors and cytokines that regulate later stages of ILC differentiation (reviewed in (Diefenbach et al., 2014)), that would act on ILCP to induce development of a particular ILC subset. Alternatively, stochastic expression of cytokine receptors may provide a fraction of ILCP with the ability to further differentiate. A better understanding of the mechanisms that regulate ILCP responsiveness within different tissue environments will be critical for potential therapeutic applications in human disease.

The inventors' studies highlight the important role for Notch signals in regulating human ILC differentiation from uni-potent and multi-potent ILCP. ILCP from tissues and in blood show a greater multi-potency in the presence of Notch signals (OP9-DL4 culture system). This may indicate a higher dependence of multi-potent ILCP for Notch-dependent survival and proliferative signals (Chea et al., 2016b). Alternatively, particular ILC subsets may be more Notch-dependent in terms of their homeostasis. In particular, $NCR^+$ ILC3 subsets in mice are Notch-dependent (Chea et al., 2016a), although the mechanism of action remains unclear. The increased frequency of IL-17A and IL-22-producing cells in OP9-DL4 cultures at the bulk and clonal levels may reflect a similar requirement in the human system.

The inventors' analysis of human fetal liver provides the first evidence for multi-potent ILCP and ILC3-restricted progenitors during gestation. It was remarkable that other uni-potent ILCP were rarely detected in this tissue, suggesting that at this stage of fetal development, the liver microenvironment may deliver signals that strongly polarize ILCP towards ILC3. In the mouse, similar findings have been reported (Cherrier et al., 2012). Notch signals have been proposed to play a role in directing lymphoid cell fate decisions in the mouse fetal liver, promoting the development of T-lineage primed precursors but also modifying homeostasis of ILCP (Chea et al., 2016b; Dallas et al., 2005). Soluble factors are also likely to be involved as ILCP express several cytokine receptors (IL-1R, IL-2R, IL-18R) that allow them to sense tissue inflammation and stress.

Regulation of TF expression dictates ILC fate as well as function. Signature TF have been identified for ILC subsets that 'fix' their differentiation at the level of surface phenotype and effector outputs, especially for cytokines (reviewed in (Serafini et al., 2015)). The TF RORC helps define the ILC3 subset and is required for development and maintenance of ILC3 (but not ILC1, ILC2 or NK cells) in mice (Luci et al., 2009; Sawa et al., 2010). As expected, RORC is expressed by human ILC3 and in committed ILC3P (Montaldo et al., 2014). The recent report that all human ILC subsets express RORC (Scoville et al., 2016) suggested a broader role for this TF in human ILC differentiation. By analyzing blood from RORC-deficient patients, the inventors could show that RORC was not required for global ILC differentiation in humans, but rather was critical for the differentiation of the IL-17 ILC3 subset. ILCP in RORC-deficient patients retained the capacity to generate other ILC and NK cell subsets. Interestingly, IL-22$^+$ ILC3 developed in a RORC-independent fashion, suggesting compensatory pathways for these cells in humans.

The use of OP9 stroma was already shown to minimize human ILC2 plasticity (Lim et al., 2016) and here the inventors show that the vast majority of NKp44+ ILC3 clones retain their functional attributes and show little plasticity towards the ILC1 phenotype in this culture system. Moreover, previous reports proposed that ILC1 clones rapidly differentiate towards an ILC3 fate in the presence of IL-1b (Bernink et al., 2015), whereas ILC1 clones in the inventors' OP9 culture system (containing IL-1β) retained their IFN-γ signature. As such, the inventors' culture system appears useful to assess signals that promote 'primary' ILC fate from ILCP.

Finally, the inventors' identification of circulating and tissue-resident human ILCP suggests a concept of 'ILC-poiesis on-demand' in which ILC differentiation can occur in any tissue and at any age. A recent study using parabiosis in mice has proposed that ILCs are long-lived tissue-resident cells that do not recirculate under steady-state and some inflammatory conditions (Gasteiger et al., 2015). In contrast, other reports have indicated that the half-life of several mucosal ILC subsets is on the order of weeks, suggesting that these cells must be renewed (Sawa Science). The discovery of a circulating ILCP provides a mechanism to replenish tissue ILCs in response to steady-state losses and in the context of infection and inflammation. The invention encompasses compositions comprising and methods of making and using ILCPs.

Compositions Comprising ILCPs

The invention encompasses compositions comprising innate lymphoid cell precursors (ILCPs) as described herein. All of the markers used herein (e.g., in the Examples) are specifically contemplated in any and all combinations for use as markers of ILCPs and can be used in various embodiments of the invention.

In one embodiment, the invention encompasses a purified population of innate lymphoid cell precursors (ILCPs). Preferably, at least 25%, 35%, 50%, 60%, 75%, 80%, 85%, 90%, 95%, or 99% of the cells in the population have the phenotype CD34-CD7+CD127+CD117+CD45RA+. Preferably, at least 25%, 35%, 50%, 60%, 75%, 80%, 85%, 90%, 95%, or 99% of the cells in the population lack the expression of NKp44 and/or RORγt. Preferably, at least 25%, 35%, 50%, 60%, 75%, 80%, 85%, 90%, 95%, or 99% of the cells in the population are IL-1R1+ and/or CD69-. More preferably, at least 25%, 35%, 50%, 60%, 75%, 80%, 85%, 90%, 95%, or 99% of the cells in the population have the phenotype CD34-CD7+CD127+CD117+CD45RA+, lack the expression of NKp44 and/or RORγt, and are IL-1R1+ and/or CD69-. More preferably, at least 25%, 35%, 50%, 60%, 75%, 80%, 85%, 90%, 95%, or 99% of the cells in the population have the phenotype Lin–CD34-CD7+CD127+CD117+CD45RA+, lack the expression of NKp44 and/or RORγt, and are IL-1R1+ and/or CD69-, and optionally further express CD62L and/or CD26.

Preferably, at least 25%, 35%, 50%, 60%, 75%, 80%, 85%, 90%, 95%, or 99% of the cells in the population are Lin–CD7+CD127+CD117+.

In some embodiments, at least 25%, 35%, 50%, 60%, 75%, 80%, 85%, 90%, 95%, or 99% of the cells in the population are Lin–CD7+CD127+CD117+CRTh2–.

In some embodiments, at least 25%, 35%, 50%, 60%, 75%, 80%, 85%, 90%, 95%, or 99% of the cells in the population are Lin–CD94– CRTh2–CD127+CD117+.

Most preferably, at least 25%, 35%, 50%, 60%, 75%, 80%, 85%, 90%, 95%, or 99% of the cells in the population are CD127+CD117+CD3–CRTh2–. In some embodiments, at least 25%, 35%, 50%, 60%, 75%, 80%, 85%, 90%, 95%, or 99% of the cells in said population are further CD7+, NKp44–, CD94–, and/or Lin–, and/or further CD26+, and/or CD62L+. In some embodiments of the method, at least 25%, 35%, 50%, 60%, 75%, 80%, 85%, 90%, 95%, or 99% of the cells in the population are CD127+CD117+Lin– CRTh2– (wherein Lin– comprises CD3–), and optionally further CD7+, NKp44–, and/or CD94–, and/or optionally further CD26+ and/or CD62L+. Preferably, at least 75%, 80%, 85%, 90%, 95%, or 99% of the cells in the population are CD127+CD117+Lin–CRTh2– (wherein Lin– comprises CD3–), and optionally further CD7+, NKp44–, and/or CD94–, and/or optionally further CD26+ and/or CD62L+. In some preferred embodiments, at least 90% of the cells in the population have the phenotype CD127+CD117+Lin– CRTh2–CD7+ or CD127+CD117+Lin–CRTh2–CD94–, and optionally CD26+ and/or CD62L+; more preferably at least 99% or 100% of the cells in the population have the phenotype CD127+CD117+Lin–CRTh2–CD94–, and optionally CD26+ and/or CD62L+. Preferably, at least 25%, 35%, 50%, 60%, 75%, 80%, 85%, 90%, 95%, or 99% of the cells in the population do not produce IL-17A or IL-22 after stimulation under conditions that these cytokines are produced by gut CD117+ cells.

Preferably, at least 25%, 35%, 50%, 60%, 75%, 80%, 85%, 90%, 95%, or 99% of the cells in the population do not express T-BET, EOMES, and GATA-3$^{hi}$.

Preferably, at least 25%, 35%, 50%, 60%, 75%, 80%, 85%, 90%, 95%, or 99% of the cells in the population do not express CD94, CD244, and CRTh2.

Preferably, at least 25%, 35%, 50%, 60%, 75%, 80%, 85%, 90%, 95%, or 99% of the cells in the population do not produce IL-13 or IFN-γ after stimulation with pharmacological activators.

Preferably, the population of cells comprises at least $10^4$, $10^5$, $10^6$, $10^7$, $10^8$, $10^9$, or $10^{10}$ ILCPs cells.

Methods for Making ILCPs

The invention encompasses methods for making a purified population of innate lymphoid cell precursors (ILCPs) of the invention. In one embodiment, the method comprises providing a human cell sample, and selecting for ILCPs in the sample. The ILCPs can be selected with any combinations of the markers set forth herein (e.g. Examples). In one embodiment, the cells are selected for any combination of the following markers Lin−, CD34−CD7+CD127+CD117+CD45RA+, NKp44−, RORγt−, IL-1R1+, CD69−, CD62L+, CD26+; in particular, Lin−, CD34−CD7+CD127+CD117+CD45RA+, NKp44−, IL-1R1+, CD69−, CD62L+, CD26+. Lin− refers to lineage negative cells; Lin− includes and refers to CD3−, CD4−, CD5−, TCRαβ−, TCRαβ−, CD14− and CD19−. Selection can be performed by routine techniques in art, such as by FACS analysis and cell sorting, for example, as described in the Examples.

In some embodiments, the cells are selected for lack of production of IL-17A or IL-22 after stimulation under conditions that these cytokines are produced by gut CD117+ cells.

In some embodiments, the cells are selected for lack of expression of T-BET, EOMES, and GATA-3hi.

In some embodiments, the cells are selected for lack of expression of CD94, CD244, and CRTh2.

In some embodiments, the cells are selected for lack of production of IL-13 or IFN-γ after stimulation with pharmacological activators, for example as described in the Examples.

In some embodiments, the sample is a blood or tissue sample. The sample can be an adult or fetal sample. In some embodiments, the sample is a blood, tonsil, gut, fetal liver, or lung sample.

In some embodiments, the cell sample is selected for Lin−CD7+CD127+CD117+CRTh2− cells, such as by cell sorting. In some embodiments, the cell sample is selected for Lin−CD94− CRTh2−CD127+CD117+ cells. In some embodiments, the cell sample is selected for CD127+CD117+CD3−CRTh2− cells. In some embodiments, the cell sample is selected for CD127+CD117+CD3−CRTh2− cells and further for CD7+, NKp44−, CD94−, and/or Lin− cells, and/or further for CD26+ and/or CD62L+ cells. In some preferred embodiments, the cell sample is selected for CD127+CD117+Lin−CRTh2− cells (wherein Lin− comprises CD3−), and optionally further for CD7+, NKp44−, and/or CD94− cells, and/or optionally further for CD26+ and/or CD62L+ cells. Preferably, the cell sample is selected for CD127+CD117+Lin−CRTh2−CD7+ or CD127+CD117+Lin−CRTh2−CD94− cells, and optionally further for CD26+ and/or CD62L+ cells; more preferably, the sample is selected for CD127+CD117+Lin−CRTh2−CD94− cells, and optionally further for CD26+ and/or CD62L+ cells. Routine techniques in the art, such as those set forth in the examples, can be used to select these cells. In preferred embodiments, cells are sorted using well-known methods in the art. In some embodiments, FACS or MACS® Technology (Miltenyi Biotech) are used to isolate particular cell types. Antibodies against any of the markers described herein can be used to achieve isolation, purification, and/or detection of any of the cell markers described herein.

Methods for Expanding ILCP

The invention encompasses methods for ILCP proliferation be added. A robust proliferation of the cells is observed when they are cultured with IL-1ß. For the proliferation of ILCP, the culture medium comprises IL-1ß and preferably IL-1ß and IL-2. Furthermore, the medium can optionally comprises other cytokines, such as IL-7.

The cells can be grown as set forth in the examples, (e.g., Example 3) or by other similar techniques. For example, ILC can be cultured in Yssel's medium with Human AB serum, Stromal cells, IL-7, IL-2, and IL-1β can be used. Alternatively, other media, such as DMEM, IMDM, or RPMI-1640, can be used. Media and/or media supplements can be varied as known in the art for cell culture. Also contemplated is supplementation of cell culture medium with mammalian sera.

The media preferably contains a serum selected from bovine serum, calf serum, fetal calf serum, newborn calf serum, goat serum, horse serum, human serum, chicken serum, porcine serum, sheep serum, rabbit serum, and rat serum, or a serum replacement or embryonic fluid. Additional supplements, such as amino acids, can be added to the medium. Antibiotics and antimycotics can also be added to the medium Methods for Making ILC1, ILC2, ILC3, and NK Cells The invention encompasses methods for making ILC1, ILC2, ILC3, and NK cells. ILC1, ILC2, ILC3, and NK cells can be produced from the ILCPs of the invention by routine techniques in the art. For example, ILC1, ILC2, ILC3, and NK cells can be produced using the specific techniques disclosed in the Examples. In one embodiment, a cell system (e.g., the OP9 stromal cell system disclosed in Mohtashami, et al. (2010)) can be used to generate ILC1, ILC2, ILC3, and NK cells from the ILCPs of the invention. Most preferably, the cells expand without changes in phenotype or function also termed "plasticity."

In various embodiments, the ILCPs are treated with various cytokines to promote differentiation into ILC1, ILC2, ILC3, and NK cells. These cytokines include any and all combinations of IL-1β (IL-1 beta), IL-12, IL-18, IL-25, IL-33, IL-23, IL-2, and IL-7.

In various embodiments, ILC subsets can be expanded using a stromal cell-based approach. While others have also shown that mature ILC can be expanded in vitro, the inventors' results are different since in that case the cells expand without 'plasticity' (change in effector function, especially for cytokine production such as IFN-γ). This plasticity can be driven by a particular human cytokine (IL-12) as the inventors showed in an earlier publication for ILC2 (Lim et al, J Exp Med 2016). ILC3 subsets can be expanded in vitro with minimal plasticity using the same approach. This approach can be used to grow large quantities of mature ILC2 or ILC3 without changing their functional properties.

ILC subsets can be expanded from ILC subsets generated from isolated ILCPs or from ILC subsets directly isolated from patient samples.

The cells can be grown as set forth in the examples or by other similar techniques. For example, ILC can be cultured in Yssel's medium with Human AB serum, Stromal cells, IL-7, IL-2, and IL-1β can be used. Alternatively, other media, such as DMEM, IMDM, or RPMI-1640, can be used. Media and/or media supplements can be varied as known in the art for cell culture. Also contemplated is supplementation of cell culture medium with mammalian sera.

The media preferably contains a serum selected from bovine serum, calf serum, fetal calf serum, newborn calf serum, goat serum, horse serum, human serum, chicken serum, porcine serum, sheep serum, rabbit serum, and rat serum, or a serum replacement or embryonic fluid. Additional supplements, such as amino acids, can be added to the medium. Antibiotics and antimycotics can also be added to the medium.

Most preferably, a medium containing IL-7, IL-2, and IL-1 is used.

Human ILCPs have been expanded in vitro using cytokines in the absence of stromal cells. Other cell lines can be used for culturing ILCP.

Preferred cell sources of ILCP are peripheral blood, but can also include bone marrow, tonsils, lymph nodes, skin, adipose tissue, gut, liver and lung. ILCPs from all of these different tissues can be cultured in vitro and give rise to mature ILC subsets.

Particular growth factor combinations can be added to the culture medium to differentiate the ILCP into a specific subset. For example, IL-12 and IL-18 can be added to generate the ILC1 subset. IL-25 and IL-33 can be added to generate the ILC2 subset. IL-23 can be added to generate the ILC3 subset.

Particular growth factor combinations can be added to the culture medium to inhibit differentiation of the ILCP into a specific subset. For example, small molecules, chemical agents or genetic modifications that alter Tbet or TBX21 expression can be used to inhibit differentiation into the ILC1 subset. Small molecules, chemical agents or genetic modifications that alter BCL11B expression can be used to inhibit differentiation into the ILC2 subset. Small molecules, chemical agents or genetic modifications that alter RORγt (RORC in mouse) expression can be used to inhibit differentiation into the ILC3 subset.

The OP9 cell line is available through ATCC (open access). OP9 cells have been used previously to develop early human T cell precursors, for example in U.S. Pat. Nos. 8,772,028 and 9,533,009.

The method for expanding ILC3 with minimal plasticity differs from that described for ILC2 in the Lim et al. J Exp Med 2016. For ILC2, mature ILC2 (isolated from blood) were cultured (on OP9) with IL-2, IL-7, IL-25 and IL-33. For ILC3, mature ILC3 are cultured with IL-2, IL-7 and IL-1. (see Example 3 where mature ILC3 are isolated from tonsils and cultured on OP9-DL4 with IL-2, IL-7 and IL-1β)

In addition to tonsils, the procedure to generate ILC3 has been successfully used with fetal liver, cord blood, adult peripheral blood, lung, fat and gut samples.

Either the ILCPs or the ILC1, ILC2, or ILC3 cells could also be modified by CRISPR, ZFNs, or TALENs, or other genomic editing technologies to add or eliminate desired genomic sequences. Vectors, including retroviral, AAV, and lentiviral vectors, can also be used to modify these cells. In various embodiments, a gene selected from RORC or RORγt, BCL11B, Tbet, and TBX21 is inactivated.

The cells can also be modified to contain a chimeric antigen receptor (CAR). These CARs typically comprise a single-chain binding domain, such as from a monoclonal antibody or nanobody, fused to a transmembrane domain and endodomain that results in the transmission of a signal in response to binding of the binding domain to its target. Examples of CARs are well-known in the art. Such a genetically-engineered receptor, can be used to graft the specificity of a monoclonal antibody onto a mature ILC. ILCs expressing CARs may be useful in some autoimmune diseases since some subsets of ILCs (e.g. ILC2) suppress immune responses through myeloid cells.

In various embodiments, the ILCPs are administered in vivo to promote differentiation into ILC1, ILC2, ILC3, and NK cells.

In various embodiments, the method comprises providing a population of innate lymphoid cell precursors (ILCPs), subjecting the cell population to an external stimulus, and detecting an increase in at least one cell type selected from ILC1, ILC2, ILC3, and NK cells. In various embodiments, the ILC1, ILC2, ILC3, and/or NK cells are separated, purified, and/or harvested.

The cell population can be subjected to an external stimulus in vivo or in vitro. In some embodiments, the cell population is subjected to an external stimulus in a humanized mouse model. In various embodiments, the external stimulus is a viral, parasitic, microbial, or bacterial organism (e.g. HIV or malaria) or a component thereof (e.g., DNA or protein). In various embodiments, the external stimulus is a cytokine or mixture of cytokines. In various embodiments, the external stimulus is a test compound.

Preferably, at least 25%, 35%, 50%, 60%, 75%, 80%, 85%, 90%, 95%, or 99% of the cells in the population have the phenotype CD34−CD7+CD127+CD117+CD45RA+, lack the expression of NKp44 and RORγt, and/or are IL-1R1+ and CD69−, and optionally further express CD62L and/or CD26. Preferably, at least 25%, 35%, 50%, 60%, 75%, 80%, 85%, 90%, 95%, or 99% of the cells in the population have the phenotype Lin−CD34−CD7+CD127+ CD117+CD45RA+, lack the expression of NKp44 and RORγt, and/or are IL-1R1+ and CD69−, and optionally further express CD62L and/or CD26.

In some embodiments, at least 25%, 35%, 50%, 60%, 75%, 80%, 85%, 90%, 95%, or 99% of the cells in the population are Lin−CD7+CD127+CD117+CRTh2−. Preferably, at least 75%, 80%, 85%, 90%, 95%, or 99% of the cells in the population are Lin−CD7+CD127+CD117+CRTh2−; more preferably, at least 90%, 95%, or 99% of the cells in the population are Lin−CD7+CD127+CD117+CRTh2−.

In some embodiments, at least 25%, 35%, 50%, 60%, 75%, 80%, 85%, 90%, 95%, or 99% of the cells in the population are Lin−CD94−CRTh2−CD127+CD117+. Preferably, at least 75%, 80%, 85%, 90%, 95%, or 99% of the cells in the population are Lin−CD94−CRTh2− CD127+ CD117+; more preferably, at least 90%, 95%, or 99% of the cells in the population are Lin−CD94− CRTh2−CD127+ CD117+; still more preferably at least 99% or 100% of the cells in the population are Lin−CD94−CRTh2−CD127+ CD117+.

Preferably, at least 25%, 35%, 50%, 60%, 75%, 80%, 85%, 90%, 95%, or 99% of the cells in the population are CD127+CD117+CD3−CRTh2−. More preferably, at least 25%, 35%, 50%, 60%, 75%, 80%, 85%, 90%, 95%, or 99% of the cells in the population are CD127+CD117+CD3− CRTh2− and further CD7+, NKp44−, CD94−, and/or Lin−, and/or further CD26+, and/or CD62L+. In some embodiments of the method, at least 25%, 35%, 50%, 60%, 75%, 80%, 85%, 90%, 95%, or 99% of the cells in the population are CD127+CD117+Lin−CRTh2− (wherein Lin− comprises CD3−), and optionally further CD7+, NKp44−, and/or CD94−, and/or optionally further CD26+ and/or CD62L+. Preferably, at least 75%, 80%, 85%, 90%, 95%, or 99% of the cells in the population are CD127+CD117+Lin−CRTh2− (wherein Lin− comprises CD3−), and optionally further CD7+, NKp44−, and/or CD94−, and/or optionally further CD26+ and/or CD62L+. In some preferred embodiments, at least 90% of the cells in the population have the phenotype CD127+CD117+Lin−CRTh2−CD7+ or CD127+CD117+ Lin−CRTh2−CD94−, and optionally CD26+ and/or CD62L+; more preferably at least 99% or 100% of the cells in the population have the phenotype CD127+CD117+Lin− CRTh2−CD94−, and optionally CD26+ and/or CD62L+.

Methods and Compositions for Treatment

The invention encompasses compositions comprising innate lymphoid cell precursors (ILCPs) for use to treat patients in need of innate immune system regulation. Thus, the invention encompasses the use of these compounds to treat patients and the methods for treating them.

In various embodiments, the patients have a helminth infection, enteric pathogen infection, tumor, viral infection, allergy, asthma, inflammation or autoimmune disease (e.g., multiple sclerosis, systemic lupus erythematosus, or type I diabetes mellitus).

In various embodiments, the patients can be immune deficient, immunocompromised, or immune suppressed. In various embodiments, the patient is a cancer patient or has a chronic disease (e.g. Crohn's disease, IBD).

In various embodiments the invention encompasses a method for treatment of a human patient comprising administering to the patient a purified population of ILCPs, wherein at least 90% of the cells in the population have the phenotype CD34−CD7+CD127+CD117+CD45RA+, lack the expression of NKp44 and RORγt, and/or are IL-1R1+ and CD69−, and/or optionally CD26+, and/or CD62L+.

In various embodiments the invention encompasses a method for treatment of a human patient comprising administering to the patient a purified population of ILCPs, wherein at least 90% of the cells in the population have the phenotype Lin−CD34−CD7+CD127+CD117+CD45RA+, lack the expression of NKp44 and RORγt, and/or are IL-1R1+ and CD69−, and/or optionally CD26+, and/or CD62L+. In some embodiments, at least 90%, 95%, or 99% of the cells in the population are Lin−CD7+CD127+CD117+CRTh2−. In some embodiments, at least 90%, 95%, or 99% of the cells in the population are Lin−CD94−CRTh2−CD127+CD117+.

Preferably, at least 90%, 95%, or 99% of the cells in the population are CD127+CD117+CD3−CRTh2−. More preferably, at least 90%, 95%, or 99% of the cells in the population are CD127+CD117+CD3−CRTh2− and further CD7+, NKp44−, CD94−, and/or Lin, and/or further CD26+ and/or CD62L+. In some preferred embodiments, at least 90%, 95%, or 99% of the cells in the population are CD127+CD117+Lin−CRTh2− (wherein Lin− comprises CD3−), and optionally further CD7+, NKp44−, and/or CD94−, and/or optionally further CD26+ and/or CD62L+. Preferably, at least 90% of the cells in the population have the phenotype CD127+CD117+Lin−CRTh2−CD7+ or CD127+CD117+Lin−CRTh2−CD94−, and optionally CD26+ and/or CD62L+; more preferably at least 99% or 100% of the cells in the population have the phenotype CD127+CD117+Lin−CRTh2−CD94−, and optionally CD26+ and/or CD62L+.

In various embodiments, uni-potent and multi-potent ILCP, especially multi-potent ILCP, can be combined with appropriate factors to make them differentiate in vitro or in vivo, into a specific type (ILC1, ILC2 or ILC3), depending on the disease to be treated. In some embodiments, it may be beneficial to either augment or inhibit differentiation of ILCP or to inhibit differentiation into a specific type, depending on the disease (See, e.g., WO2016/138590, US2016/0145344, and US2016/0304574, which are hereby incorporated by reference).

ILC subsets are involved in various diseases and cellular processes, including infections, cancer inflammation, tissue repair, and homeostasis. Tait Wojne et al, 2016, which is incorporated by reference herein. Since ILC3s promote GALT formation, inflammation, immunity, and homeostasis in the intestine (id.), ILC3s generated by the methods of the invention can be used to treat diseases involving these processes. Since ILC2s influence inflammation, immunity, tissue repair, and homeostasis through interactions with hematopoietic and nonhematopoietic cells (id.), ILC2s generated by the methods of the invention can be used to treat diseases involving these processes. Since ILC1s express T-bet and IFN-γ and contribute to type 1 inflammation (id.), ILC1s generated by the methods of the invention can be used to treat diseases involving these processes.

The cells can be administered to the patient by routine techniques in the art. Preferably, $10^4$, $10^5$, $10^6$, $10^7$, $10^8$, $10^9$, or $10^{10}$ ILCPs cells are administered to the patient. Autologous, allogeneic, or xenogeneic ILCs or ILCPs can be administered to a subject, preferably a human, by direct injection into a tissue or blood, etc. Preferably, the cells are administered in combination with a pharmaceutically acceptable carrier. The cells can be administered in a single or at least 2, 3, 4, 5, etc. injections. The cells can be genetically modified to alter their immune recognition.

Screening Methods Using ILCPs

The invention encompasses methods for screening for compounds that modulate (i.e., inhibit or enhance) the differentiation of ILCPs into ILC1, ILC2, ILC3, and/or NK cells. In various embodiments, a population of the ILCPs of the invention is contacted in vivo or in vitro with a test compound and the effect of the compound on differentiation is assessed. The effect can be observed by detecting a change in the phenotypes of the cells in the cell population.

The test compound can be a natural compound or a synthetic compound. In various embodiments, the test compound is a viral, parasitic, microbial, or bacterial organism (e.g. HIV or malaria) or a component thereof (e.g., DNA or protein). In various embodiments, the test compound is a cytokine or mixture of cytokines.

In some embodiments, a change in the phenotypes of the cells in the cell population is detected by measuring the levels of ILCPs, ILC1, ILC2, ILC3, and/or NK cells in the cell population before and after contact with the test compound. The phenotypes of the cells can be detected as disclosed in the Examples and by similar techniques known to the skilled artisan. In some embodiments, the levels of ILCPs, ILC1, ILC2, ILC3, and/or NK cells after contact with the test compound is compared to an untreated ILCP control.

In one embodiment, the invention encompasses a method for screening for compounds that affect the development of ILCs comprising providing a population of innate lymphoid cell precursors (ILCPs), contacting the cell population with a test compound, and detecting a change in the phenotypes of the cells in the cell population.

In some embodiments, the test compound causes a reduction in the differentiation of the ILCPs. In some embodiments, the test compound causes an increase in the differentiation of the ILCPs. In some embodiments, the test compound causes a reduction in the differentiation into a specific ILC subset. In some embodiments, the test compound causes an increase in the differentiation into a specific ILC subset.

In some embodiments, the method comprises combining the ILCPs with a stimulus capable of differentiating them (e.g., OP9-DL4 culture system) and contacting the cell population with the test compound to determine the effect of the compound on differentiation. In other embodiments, the effect of the compound is determined in the absence of such a stimulus and/or with the addition of other compounds or stimuli (e.g. cytokines).

In some embodiments, the method comprises infusing a mouse with the population of innate lymphoid cell precursors (ILCPs) and administering the test compound to the mouse. Preferably, the mouse is a humanized mouse.

Preferably, at least 25%, 35%, 50%, 60%, 75%, 80%, 85%, 90%, 95%, or 99% of the cells in the population have the phenotype CD34−CD7+CD127+CD117+CD45RA+, lack the expression of NKp44 and RORγt, and are IL-1R1+ and CD69−, and/or optionally CD26+, and/or CD62L+.

Preferably, at least 25%, 35%, 50%, 60%, 75%, 80%, 85%, 90%, 95%, or 99% of the cells in the population have the phenotype Lin−CD34−CD7+CD127+CD117+CD45RA+, lack the expression of NKp44 and RORγt, and are IL-1R1+ and CD69−, and/or optionally CD26+, and/or CD62L+.

In some embodiments, at least 25%, 35%, 50%, 60%, 75%, 80%, 85%, 90%, 95%, or 99% of the cells in the population are Lin−CD7+CD127+CD117+CRTh2−.

In some embodiments, at least 25%, 35%, 50%, 60%, 75%, 80%, 85%, 90%, 95%, or 99% of the cells in the population are Lin−CD94−CRTh2−CD127+CD117+. Most preferably, at least 25%, 35%, 50%, 60%, 75%, 80%, 85%, 90%, 95%, or 99% of the cells in the population are CD127+CD117+CD3−CRTh2−. In some embodiments, at least 25%, 35%, 50%, 60%, 75%, 80%, 85%, 90%, 95%, or 99% of the cells in said population are further CD7+, NKp44−, CD94−, and/or Lin−, and/or further CD26+, and/or CD62L+. In some embodiments, at least 25%, 35%, 50%, 60%, 75%, 80%, 85%, 90%, 95%, or 99% of the cells in the population are CD127+CD117+Lin−CRTh2− (wherein Lin− comprises CD3−), and optionally further CD7+, NKp44−, and/or CD94−, and/or optionally further CD26+ and/or CD62L+. Preferably, at least 75%, 80%, 85%, 90%, 95%, or 99% of the cells in the population are CD127+CD117+Lin−CRTh2− (wherein Lin− comprises CD3−), and optionally further CD7+, NKp44−, and/or CD94−, and/or optionally further CD26+ and/or CD62L+. In some preferred embodiments, at least 90% of the cells in the population have the phenotype CD127+CD117+Lin−CRTh2−CD7+ or CD127+CD117+Lin−CRTh2−CD94−, and optionally CD26+ and/or CD62L+; more preferably at least 99% or 100% of the cells in the population have the phenotype CD127+CD117+Lin−CRTh2−CD94−, and optionally CD26+ and/or CD62L+.

EXAMPLES

Material and Methods
Human Blood and Tissues Samples

Blood samples from healthy donors were obtained from Establishment Francais du Sang (EFS, Paris) in an agreement signed with Institut Pasteur. Blood samples from patients with RORC mutation (RORC−/−-P1; RORC−/−-P2, p.A421X/Q421X) have been previously reported (26160376). Umbilical cord blood was collected from normal deliveries. Tonsils were obtained from pediatric patients given tonsillectomy. Fetal liver was obtained from elective abortion with gestational age ranging from 14 to 20 weeks. Experiment with human fetal liver were approved by Medical and Ethical Committees at Institut Pasteur and performed in full compliance with French Law. Lungs were obtained from patients undergoing surgery and samples were provided by Dr. J M Sallenave (Hôpital Bichat). Intestinal were obtained from colon cancer patients who underwent surgery and provided by Dr. M Allez (Hôpital Saint Louis). Informed consent was obtained from each patients as requested and approved by the institutional review boards of Necker Medical School, Paris Descartes University, Hôpital Bichat, Hôpital Saint Louis, Assistance Publique—Hôpital de Paris.

Human Immune System (HIS) Mice Model

BALB/c Rag2−/−Il2rg−/−Sirpa$^{NOD}$ (BRGS) mice have been described and were maintained in isolators at Institut Pasteur. CD34$^+$ HSC or CD117$^+$ ILC were sorted from peripheral blood of healthy donors using a FACS Aria. Fetal liver CD34$^+$ HSC were isolated using CD34 Microbead Kit (Miltenyi). For in vivo transfer experiment, 1-3×10$^5$ CD117$^+$ ILC or CD34$^+$ HSC were intrahepatically injected into sublethal irradiated (3Gy) new born (3-7 days-old) BRGS mice together with 0.3 μg of IL-2 and -7 (Miltenyi). Mice were received IL-2, -7, -1β, -23, -25 and -33 (0.3 μg each) by intraperitoneal injection weekly and analyzed four weeks post-transplantation. For generation of HIS mice, fetal liver derived CD34$^+$ HSC were intrahepatically injected into sublethal irradiated (3Gy) new born (3-7 days-old) BRGS mice. Mice were sacrificed 8-9 weeks post-injection. Experiments were approved by ethical committee at Institut Pasteur and validated by French Ministry of Education and Research.

Cell Isolation from Blood, Tonsil, Gut, Fetal Liver and Lung

Human peripheral blood mononuclear cells (PBMC) from CB and PB were isolated by Ficoll-Paque (GE Healthcare) density gradient centrifugation. Single cell suspension from fetal liver and tonsil was achieved by mechanical disruption through 70-μm filters. Lung and intestine samples were minced and digested with Liberase TL (25 μg/ml; Roche) and DNase I (50 μg/ml; Sigma-Aldrich) for 45 min in 37° C. shaking incubator. Digested tissues were passed through 70-μm filters. Lymphocytes from liver, lung and gut were isolated by Ficoll-Paque density gradient centrifugation.

FACS Analysis and Cell Sorting

For FACS analysis, cells were first stained with Flexible Viability Dye eFluor 506 (eBioscience) for 10 min followed by 20 min surface antibodies staining with Brilliant Stained Buffer (BD) on ice. For experiment involving intracellular TF staining, cells were fixed, permeabilized and stained using Foxp3/Transcription Factor Staining Buffer Kit (eBioscience). For intracellular cytokines staining, cells were stimulated with PMA (Ong/ml; Sigma) plus Ionomycin (1 μg/ml; Sigma) in the presence of Golgi Plug (BD) for 3 h. Cells were fixed, permeabilized and stained by Cytofix/Cytoperm Kit (BD). Samples were acquired on LSRFortessa (BD) and analyzed by FlowJ10 (Tree Star).

For cell sorting from healthy PB, PBMC were first depleted of T cell, B cell, pDC and monocytes by labeling with biotin-conjugated anti-CD3, anti-CD4, anti-CD19, anti-CD14, anti-CD123 followed by anti-biotin microbeads (Miltenyi) according to manufacturer's instructions. Sorting from CB and tissues were performed with lineage depletion. Bulk populations were sorted to a purity ≥99% or as single cell index sorting (both using FACSAria II; BD).

Bulk RNA Isolation, Library Construction, Sequencing and Analysis

10$^3$ cells from each population were FACS sorted directly into 50 μl of lysis/binding buffer (Life Technologies). mRNA was captured with Dynabeads oligo(dT)(Life Technologies), washed and eluted at 70° C. with 10 μl of 10 mM Tris-Cl (pH7.5). A derivation of MARS-seq as described (24531970), developed for single-cell RNA-seq was used to produce expression libraries with a minimum of two replicates per population. An average of 4 million reads per library were sequenced and aligned to human reference genome (NCBI) using TopHat v2.0.10 with default parameter (Ser. No. 19/289,445). Expression levels were calculated and normalized for each samples to the total number of reads using HOMER software (homer.salk.edu). It was focused on highly expressed genes with 2-fold differential over the noise (8 reads) between the means of any two subtypes. KEGG analysis was done by using DAVID (Ser. No. 12/734,009).

Chromatin Immunoprecipitation and Sequencing (Chip-Seq) Using ChipMentation FACS sorted cells (20-50K) were immediately crosslinked in PBS containing 1% formaldehyde (Sigma) for 10 min at room temperature for ChIP-Seq analysis. Crosslinking was quenched by adding glycine (0.125M final concentration) followed by 5 min incubation at room temperature. Cells were placed on ice, washed with PBS and snap-frozen for storage at −80° C. Pellets were processed in parallel to minimize technical variation. Cells were resuspended in 100 µp sonication buffer (1% SDS, 10 mM EDTA, 50 mM Tris-HCl pH8 and 1×EDTA-free complete protease inhibitors; Roche) and transferred to a 0.65 ml Bioruptor sonication tube (Diagenode). After 15 min incubation on ice, cells were sonicated for 30 cycles (30 sec ON-30 sec OFF) using a Bioruptor Pico sonicator (Diagenode) to shear chromatin down to ±250 bp fragments. Chromatin was equilibrated by adding 900 µl 10× ChIP dilution buffer (0.01% SDS, 1.1% Triton X-100, 1.2 mM EDTA, 16.7 mM Tris-HCl pH8, 167 mM NaCl) and incubated overnight at 4° C. with 1 µl of H3K4Me2-specific antibody (ab32356, Abcam) or normal rabbit IgG as a negative control (sc-2027, Santa Cruz). In addition, 20 µl of protein A Dynabeads (Thermo Fisher Scientific) per IP were blocked in PBS containing 0.1% BSA (Sigma) by incubation overnight at 4° C. The next day, beads were resuspended in the original volume with ChIP dilution buffer and added to the chromatin extracts. After 2 hours of incubation at 4° C., beads were collected and washed with Low Salt buffer (0.1% SDS, 1% Triton X-100, 2 mM EDTA, 20 mM Tris-HCl pH8, 150 mM NaCl), High Salt buffer (0.1% SDS, 1% Triton X-100, 2 mM EDTA, 20 mM Tris-HCl pH8, 500 mM NaCl) and LiCl buffer (10 mM Tris-HCl pH8, 1 mM EDTA, 250 mM LiCl, 0.5% NP-40, 0.5% deoxycholic acid). Chromatin-antibody immobilized on magnetic beads were then subjected to tagmentation as recently described (Schmidl et al., 2015). Eluted DNA was purified using MinElute spin columns (Qiagen) and amplified for 8-12 cycles using Nextera PCR primers. Libraries were purified using dual (0.5×-2.0×) SPRI Ampure XP beads (Beckman Coulter), pooled (up to 10 per sequencing run) and sequenced on a NextSeq500 (Illumina) running a single-read 75 bp protocol.

ChIP-Seq Data Processing, Analysis and Visualization

Reads were demultiplexed using BaseSpace (Illumina) and aligned to the mouse genome (mm10 build) using Bowtie (Langmead, B. & Salzberg, S. L. Fast gapped-read alignment with Bowtie 2. Nat Methods 9, 357-359, doi: 10.1038/nmeth.1923 (2012)) with standard settings, removing reads that could not be uniquely mapped. Indexed and sorted bam files were parsed to HOMER (Heinz, S. et al. Simple combinations of lineage-determining transcription factors prime cis-regulatory elements required for macrophage and B cell identities. Mol Cell 38, 576-589, doi: 10.1016/j.molcel.2010.05.004 (2010)) for further analysis. Tag directories were generated for each sample with removal of duplicate reads (-tbp 1 option). BedGraph files displaying normalized counts (reads per million) were generated for direct visualization in the UCSC Genome Browser (https://genome.ucsc.edu/) using the makeUCSCfile HOMER script. H3K4Me2 enriched regions were identified using HOMER findPeaks with -region-size 1000 -minDist 2500 options. Overlapping and non-overlapping regions between two samples were identified using the intersect function of BEDTools (Quinlan, A. R. & Hall, I. M. BED-Tools: a flexible suite of utilities for comparing genomic features. Bioinformatics 26, 841-842, doi:10.1093/bioinformatics/btq033 (2010)) or the HOMER mergePeaks script (-d given option) requiring a minimal overlap of 1 bp. Sets of cell type-specific H3K4Me2+ regions were visualized as heatmaps with Java TreeView (Saldanha, A. J. Java Treeview—extensible visualization of microarray data. Bioinformatics 20, 3246-3248, doi:10.1093/bioinformatics/bth349 (2004)). Regions/peaks were assigned to putative target genes GREAT (McLean, C. Y. et al. GREAT improves functional interpretation of cis-regulatory regions. Nat Biotechnol 28, 495-501, doi:10.1038/nbt.1630 (2010)). GREAT was subsequently used to calculate enrichments of these genes for known pathway signatures using the whole genome as background.

Bulk and Single Cell Culture

All in vitro culture experiments were performed in Yssel's medium (Ser. No. 18/432,890) supplemented with 2% human AB serum (EFS). 2-3×$10^3$ stromal cells were pre-seeded in 96-well round bottom plates one night before culture. Yssel's medium is prepared in house by using IMDM (Invitrogen) plus 0.25% (w/v) bovine serum albumin (Sigma), 1.8 µg/L 2-amino ethanol, 40 µg/L Apo-transferrin, 5 g/L insulin and penicillin/Streptomycin. For bulk culture, 100-300 FACS sorted cell were plated on the stromal cells. For cloning experiment, cells were index-sorted directly into the 96-well plates pre-seeded with stromal cells. Cytokines IL-2, -7 (20 ng/ml each, Miltenyi), IL-12, -18, -25, -33, -1β, -23 (20 ng/ml each, R&D) were provided in various combinations as indicated. For bulk culture, fresh cytokines and medium were replenish every 5 days and analyzed after 10 days expansion. For cloning experiment, cytokines and medium were replenished every 7 days and analyzed after 14-18 days of culture.

Example 1: Characterization of Human Peripheral Blood CD117+ ILC

Data are represented as Median unless specified. The sample size for each experiment and the replicate number of experiments are included in the figure legends. Circulating ILC can be identified as a low frequency population (<0.2% of total CD45+ cells) within lineage CD7+CD56−CD127+ peripheral blood (PB) cells of healthy individuals as well as patients suffering from diverse clinical syndromes ((Hazenberg and Spits, 2014; Munneke et al., 2014; FIGS. 1A and 1B). Further fractionation of PB ILCs into ILC1, ILC2 and ILC3 has been achieved using phenotypic markers that identify ILC subsets in fetal tissues and tonsils, including CD161, CRTh2, CD117 and NKp44 (Spits et al., 2013). As such, previous reports have identified circulating ILC2 (CD161+CRTh2+GATA-3+ cells) as well as ILC1 (CD161+CRTh2−CD117−T-BET+ cells) in human blood (Mjösberg et al., 2011). Circulating ILCs also include a predominant CD117+ subset that lacks CRTh2 expression ((Munneke et al., 2014; Vély et al., 2016); FIGS. 1A and 1B). Previous studies have considered these cells as circulating ILC3 since tissue-resident ILC3 strongly express CD117 (Cella et al., 2009; Cupedo et al., 2009). However, it was found that PB CD117+ ILC differ dramatically from gut CD117+ ILC in that they lack expression of NKp44 and of the transcription factor (TF) RORγt that identifies ILC3 (FIG. 1C). Accordingly, PB CD117+ ILC do not produce IL-17A or IL-22 after stimulation, whereas gut CD117+ cells abundantly produce these ILC3-associated cytokines (FIG. 1D). Interestingly, circulating CD117$^+$ ILC express high levels of IL-1R1, CD45RA and are CD69$^-$, whereas gut-resident ILC3 are CD69$^+$ but IL-1R1$^-$ and CD45RA$^-$ (FIG. 1C). These observations suggest that PB CD117$^+$ ILC are not bona fide ILC3.

PB CD117$^+$ ILC did not express signature TFs that characterize other known ILC subsets (ie.: T-BET, EOMES, GATA-3$^{hi}$) (FIG. 1C). Accordingly, PB CD117$^+$ ILC failed to express markers associated with NK cells, ILC1 and ILC2, such as CD94, CD244, CRTh2 (FIG. 1A) and did not produce IFN-γ or IL-13 after stimulation with pharmacological activators (FIG. 1D). Taken together, these results suggest that PB CD117$^+$ ILC do not represent any canonical ILC subset.

Example 2: Transcription and Chromatin Landscapes of CD117$^+$ ILC Reveal an ILC Precursor Profile As CD117 is highly expressed on hemato-lymphoid progenitors (Ikuta and Weissman, 1992; Kikushige et al., 2008), it was hypothesized that PB CD117$^+$ ILC might include uncommitted lymphoid precursors. In order to further understand the identity of PB CD117$^+$ ILC, the transcriptomic and epigenetic landscapes of highly purified circulating CD117$^+$ ILC was profiled and compared to CD34$^+$ HSC (FIG. 2A); the latter representing immature hematopoietic progenitors with multi-lineage potential (Baum et al., 1992; Mohtashami et al., 2010).

Figure 2:
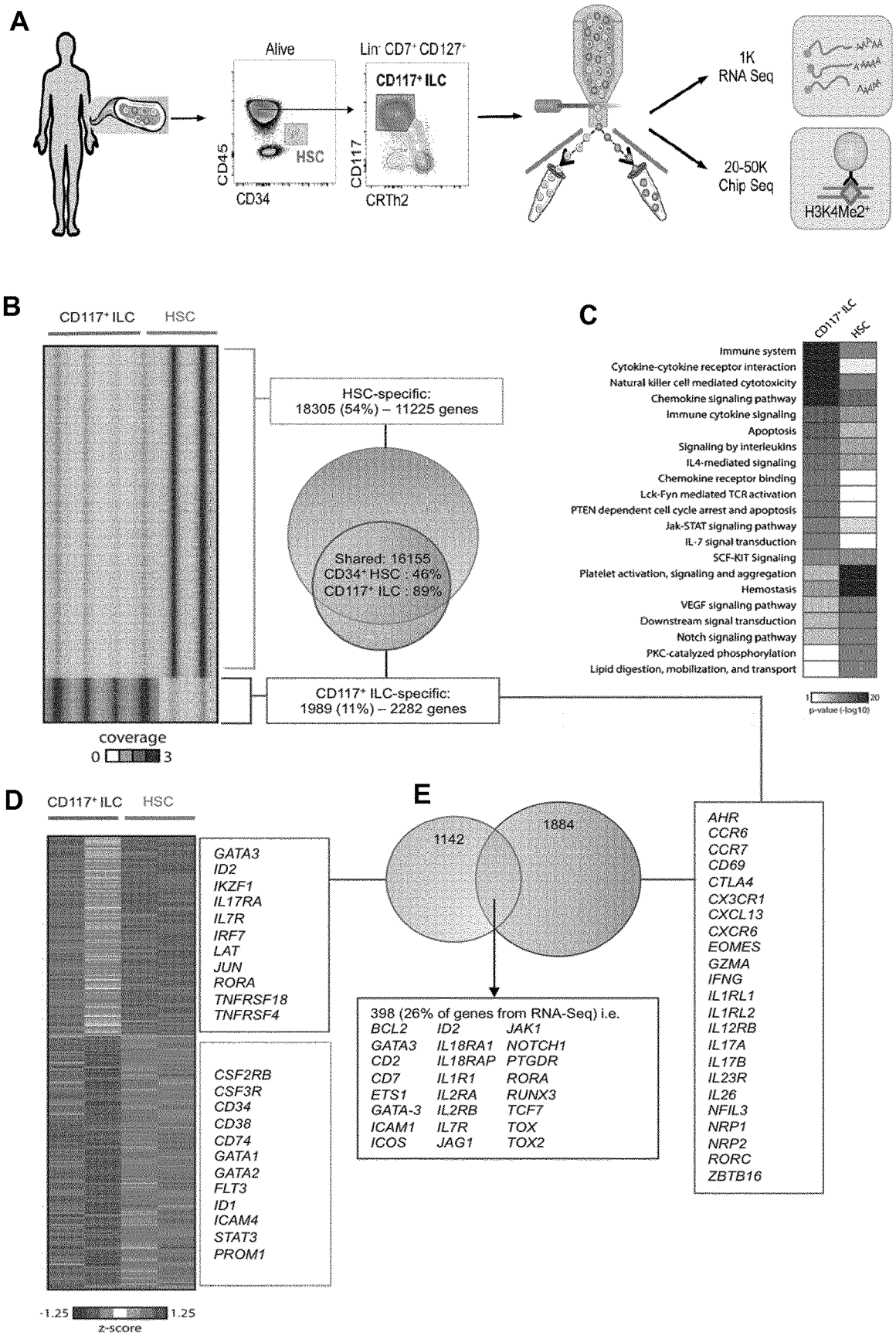
FIG. 2A-E depict the transcriptional signature and chromatin landscape of CD117+ILC. (A) Schematic and gating strategy for CD117$^+$ ILC and CD34$^+$ HSC freshly isolated from peripheral blood of healthy donor by FACS to perform bulk RNA Seq and Chip Seq. (B) Heatmap depicting normalized ChIPm-Seq signal showed H3K4me2 intensity of 36449 high-confidence enhance region that 1989 regions were specifically identify from CD117+ILC. Venn diagram showed the three categories of H3KMe2$^+$ region ('CD34$^+$ HSC-specific'; 'CD117$^+$ ILC-specific' and 'shared'). Regions were considered cell-type specific if H3K4Me2$^+$ enrichment levels differed >2-fold. (C) Heatmap of molecular pathway enrichment for genes located near GREs uniquely identified from CD117$^+$ ILC (blue) and CD34$^+$ HSC (orange). (D) Heatmap showing clustering of 1540 genes differentially expressed by CD117$^+$ ILC compared to CD34$^+$ HSC that identified by RNA seq. (E) Overlap of the 1540 genes highly expressed by CD117$^+$ ILC from RNA seq and 2283 genes identified from 'CD117$^+$ ILC-specific' H3KMe2$^+$ GREs.

Chromatin immunoprecipitation was performed followed by high-throughput sequencing using transposase-mediated tagmentation (ChIPm-Seq) that allowed the inventors to directly analyse the epigenome of small number of purified cells. To expose common and unique epigenetic features of CD34$^+$ HSC and CD117$^+$ ILC, histone H3 lysine 4 dimethylation (H3KMe2) was mapped since it marks both active and poised gene regulatory elements (GRE) with superior precision than other histone modifications (Zhang et al. 2012 Cell, Koche et al. Cell Stem Cell 2011). Around 18,000 and 35,000 GRE were identified in CD117$^+$ ILC and CD34$^+$ HSC respectively (FIG. 2B), the majority of which were located in introns and intergenic regions (Supp. Fig. X). A significant number of H3K4Me2$^+$ GRE were shared between the two cell types: 89% of GRE identified in CD117$^+$ ILC showed similar enrichment in HSC and were associated with 13159 genes of which many encoded housekeeping functions. Nevertheless, 11% of H3K4Me2$^+$ GRE detected in CD117$^+$ ILC were absent in CD34$^+$ HSC, potentially regulating 2283 genes. Pathway analysis of these genes revealed a strong enrichment for immune system and lymphocyte related processes (FIG. 2C). For example, cytokine/chemokine signaling genes critical for lymphoid development and function such as IL1R1, IL7R, IL2RA/B were linked to a CD117$^+$ ILC-specific GRE. Conversely, GRE only active in CD34$^+$ HSC (54% of all GRE in CD34$^+$ HSC) were located near genes involved in more general pathway important for hematopoiesis, including hemostasis, platelet activation and Notch signaling pathway (FIG. 2C).

To compare the transcriptome of CD117$^+$ ILC and CD34$^+$ HSC, RNA sequencing (RNA-Seq) was performed. Clear differences in gene expression profiles emerged, with a large cluster of 1540 genes expressed at substantially higher levels in CD117$^+$ ILC (FIG. 2D). Among these were many genes strongly linked to the lymphoid lineage, including IKZF1, CD2, CD7 and IL7R (FIG. 2D). In contrast, CD34$^+$ HSC cells highly expressed genes involved in the broad development of diverse hematopoietic lineages, including ID1, GATA, GATA2 and MYB (FIG. 2D) as well as cytokine receptors for myeloid lineages (CSF3R, CSF2RB, FLT3). Compared to HSC, CD117$^+$ ILC express high levels of TF that have been shown to be essential for murine ILC development, including ID2, GATA3, TOX and TCF7. Transcripts characteristic of T and B cells development, such as RAG1, RAG2, EBF1, CD3E, BCL11A or LMO2 were not detected in CD117$^+$ ILC although some of these genes are expressed by HSC.

As both transcriptomic and epigenetic analyses of CD117$^+$ ILC identified strong lymphoid signatures, these datasets were intersected in order to gain insights into the developmental status of CD117$^+$ ILC. A substantial proportion (26%) of the genes most highly expressed in CD117$^+$ ILC were located in the direct vicinity of a CD117$^+$ ILC-specific GRE (FIG. 2E). Surprisingly, these included many transcription factors previously implicated in mouse ILC development, including ID2, GATA3, ETS1. TOX, TCF7, RORA and NOTCH1 (FIG. 2E)—consistent with the commitment of CD117$^+$ ILC to the innate lymphoid fate. In contrast, notable expression levels were not detected for any of the mature ILC TFs (EOMES, TBX21, RORC), cytokine receptors (CCR6, IL1RL1, IL23R) or signature cytokines (IFNG, IL13, IL5, IL22, IL17A). However, several of these mature ILC identity genes were already marked with H3K4Me2, demonstrating that they reside in a poised state (FIG. 2E). In contrast, key regulators of B and T cell development (RAG1, RAG2, EBF1, BCL11A, HES1, LMO2) were not selectively marked with H3K4Me2. Together, these analyses suggest that CD117$^+$ ILC represent lymphoid-biased progenitors carrying a TF expression profile resembling a multi-potent ILC precursor (ILCP) with key mature ILC signature genes in an epigenetically poised state.

Example 3: Peripheral Blood CD117$^+$ ILC Include Multi-Potent ILC Precursors (ILCP)

Figure 3:
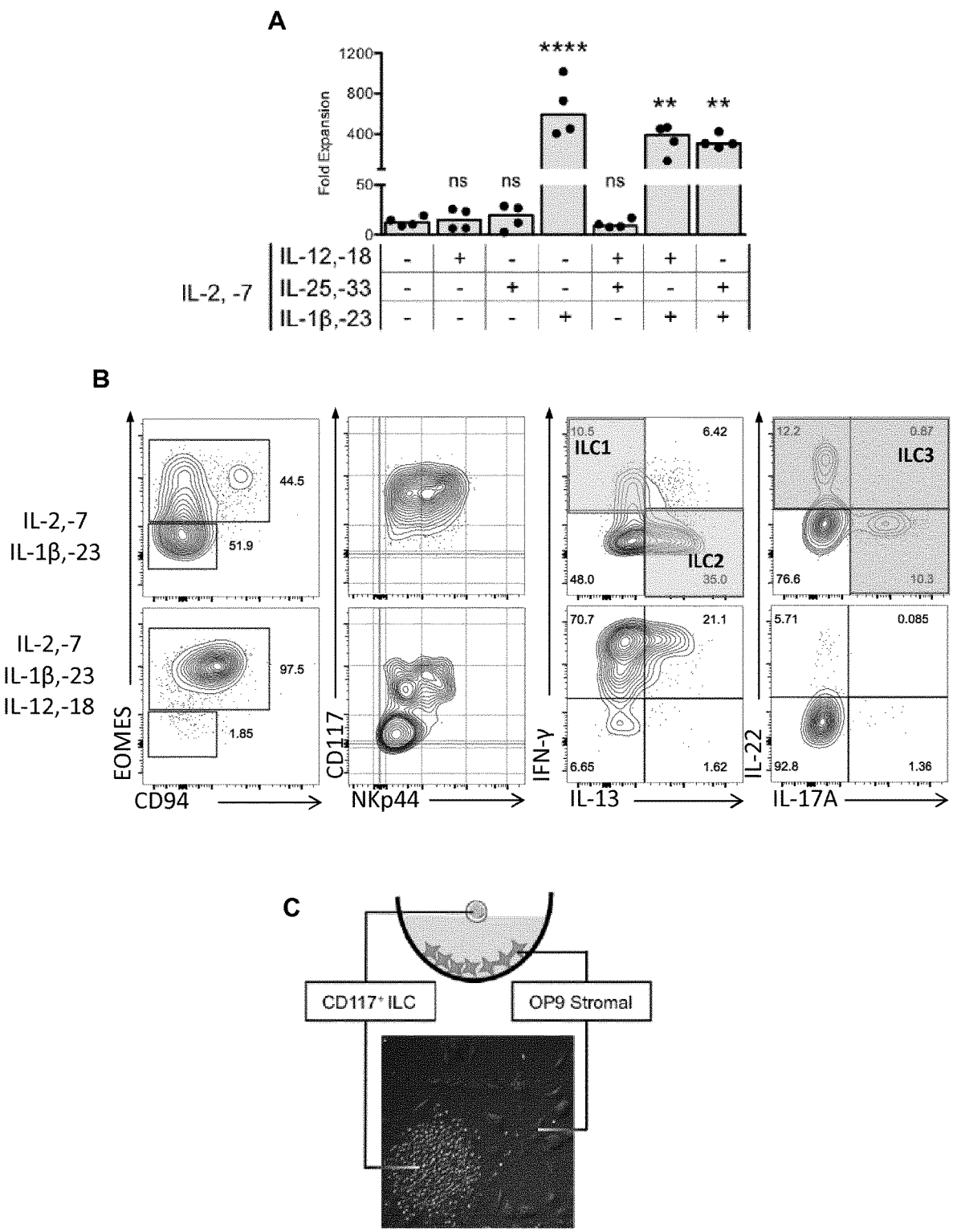
FIG. 3A-E depict that cloning reveals multi-ILC lineage potential of CD117+ILC in vitro. (A) Expansion of bulk cultured CD117$^+$ ILC (10 days) in stromal cell-free conditions with cytokines (20 ng/ml for each cytokine). Results from four independent donors; ns, P>0.05;, P<0.01; **, P<0.0001 using paired Student's t test (Median). (B) FACS analysis of bulk cultured CD117$^+$ ILC for surface phenotypes, intracellular EOMES and cytokine expression after 3 h PMA/ionomycin stimulation to identify NK cells (EOMES$^+$ cells), ILC1 (IFN-γ$^+$ cells), ILC2 (IL-13$^+$) and ILC3 (IL-22$^+$ and/or IL-17A$^+$). (C) Schematic diagram and morphology of CD117$^+$ ILC-OP9 stromal co-culture system. (D) Single PB CD117+ILC were FACS index sorting and cultured on OP9 or OP9-DL4 stromal cells for 14-18 days. Cells were stimulated with PMA/iono 3 h before analysis for surfaces and cytokines profiles. Positive clones were considered when at least 100 viable human CD45$^+$ cells were detected by FACS. Presence of an ILC subset was scored when more than 5% of corresponding cytokine was detected in total viable CD45 cells. (E) Pie chart depicting all possible ILC combinations detected. Frequency of each single or multi ILC differentiation among total positive wells. Data summarized from four independent experiments with one donor each. On average, cloning efficiency was 40% on OP9 and 26% on OP9-DL4 stromal cells.

In order to assess the hematopoietic potential of circulating CD117$^+$ ILC, these cells were bulk cultured in the presence of various cytokines. As CD117$^+$ ILC express CD25, CD127 and CD121a (IL-1R1) (FIGS. 1A, 1C), IL-2, IL-7 and/or IL-1 were added to these cultures. While bulk cultures minimally expanded in the presence of IL-2 and IL-7, robust proliferation was observed when cells were cultured in IL-1β (FIG. 3A). The additional presence of cytokines that can drive ILC1/NK (IL-12, -18), ILC2 (IL-25, -33) or ILC3 (IL-23) development did not further increase cell yield over that obtained with IL-1β (FIG. 3A). Bulk cultured cells did not harbor B (CD19$^+$) or T (CD3$^+$CD5$^+$) cells but comprised a pure population of CD7$^+$ cells that were CD161$^+$ and expressed variable levels of CD117 and CD25 (FIG. 3B).

Remarkably, expanded cells included some EOMES$^+$ CD94$^+$ NK cells as well as cells representing the three canonical ILC groups: IFN-γ$^+$ ILC1, IL-13$^+$ ILC2 and NKp44$^+$IL-17A$^+$IL-22$^+$ ILC3 (FIG. 3B). While IL-25 and IL-33 supplementation did not appreciably alter the distribution of ILC subsets in these cultures, the addition of IL-12 clearly promoted the development of EOMES$^+$CD94$^+$ IFN-γ-producing NK cells and IL-23 was critical for IL-17A-producing-ILC3 (FIG. 3B). These results not only define a cytokine 'mix' that supports multi-lineage ILC and NK cell generation (IL-2, IL-7, IL-1β, IL-23) but also suggest that PB CD117$^-$ILC harbors multi-lineage ILC precursors (ILCP).

The multi-lineage potential of circulating CD117$^+$ ILC was further characterized using a modified stromal cell-based culture system that is permissive for B cell, T cell and myeloid cell development (FIG. 3C; Mohtashami et al., 2010)). Moreover, this system can extensively expand human NK cells and ILC subsets at the clonal level with minimal plasticity (Lim et al., 2016). Progeny of single PB CD117$^+$ ILC cultured on OP9 and OP9-DL4 were analyzed to identify EOMES$^+$ NK cells and ILC subsets producing IFN-$\gamma$, IL-13, IL-17A and/or IL-22 (FIG. 3D). OP9-DL4 stroma express a strong Notch ligand allowing the inventors to assess the impact of triggering this pathway (Mohtashami et al., 2010). The inventors' analysis of over 340 clonal cultures allows several points to be made. First, PB CD117$^+$ ILC represent a heterogeneous population of uni-potent and multi-potent ILC precursors (ILCP). Roughly half of the cultures derived from single CD117$^+$ ILC generate a single ILC subset (ILC1, ILC2 or ILC3 only) and therefore represent lineage-restricted ILCP, whereas the remainder are multi-potent ILCP that can give rise to 2 or more separate Lin$^-$CD7$^+$ ILC lineages (FIG. 3E). B cell and T cell potential was not observed. Second, within the multi-potent ILCP population, a substantial fraction (between 9-17%) are able to generate all three ILC subsets and likely represent immature uncommitted ILCP. Moreover, clonal IFN-$\gamma^+$ cultures also comprise EOMES$^+$ NK cells demonstrating that some PB ILCP have the potential to generate both 'helper' and 'cytotoxic' ILC lineages at the single cell level. Third, a subset of Lin$^-$CD7$^+$ ILC clones failed to produce any cytokine tested (FIG. 3E). As these clones maintained high level of CD7 and CD117 but lacked other ILC markers, they may represent ILCP that have not further differentiated. Fourth, Notch signals clearly influence the cell fate potential of CD117 ILCP as multi-potentiality and development of ILC3-containing cells was enhanced on OP9-DL4 (FIG. 3E). Together, these data identify PB CD117$^+$ ILC as a circulating pool of committed ILC progenitors. The comparison of bulk and clonal assays clearly demonstrate the importance of the single cell approach to define heterogeneity of CD117$^+$ ILC cell fate potential and to establish functional multipotency.

Figure 4:
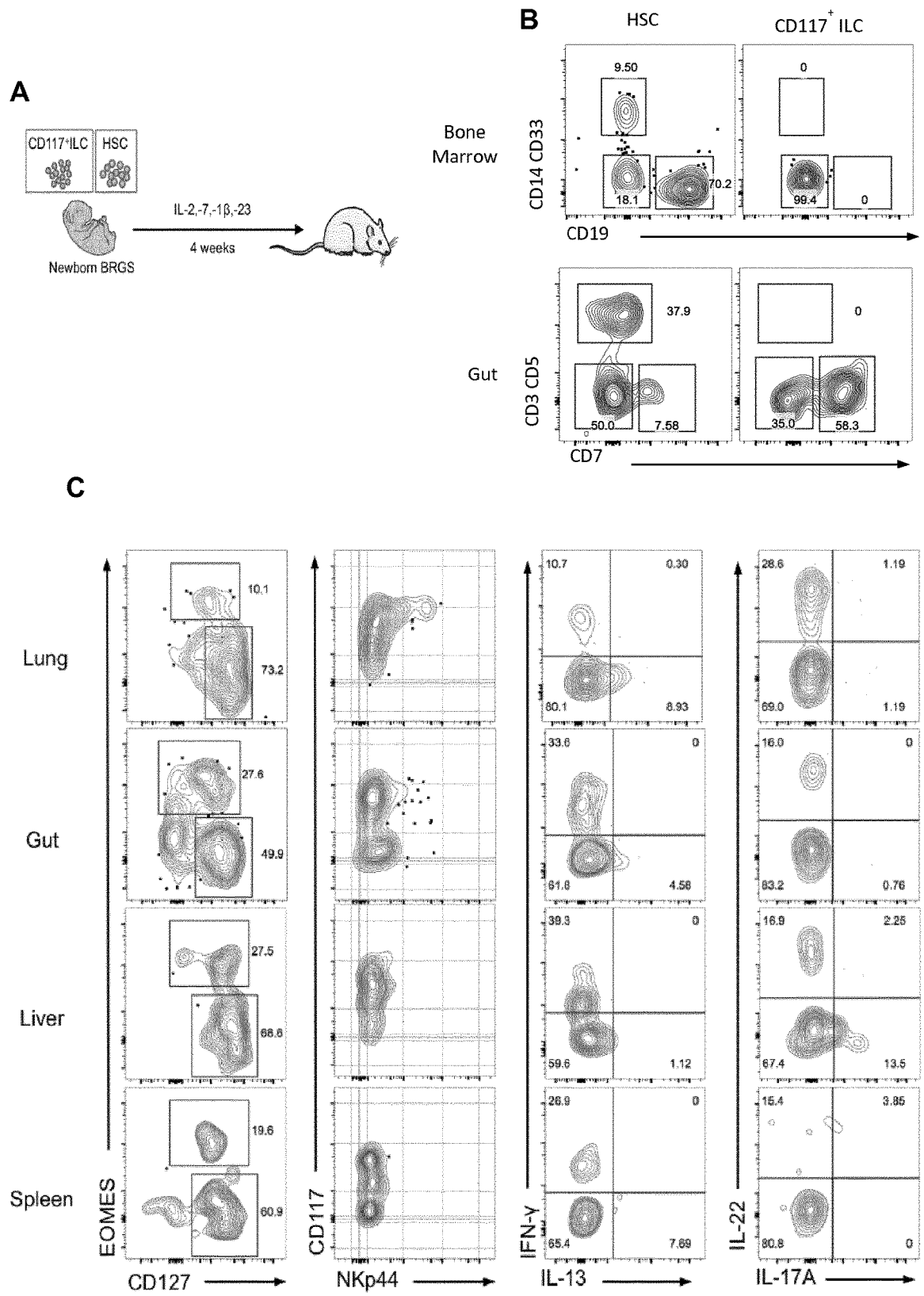
FIG. 4A-C depict that CD117+ILC effectively gives rise to multi-ILC lineage in vivo. (A) Schematic diagram of in vivo transfer experiment. (B-C) Newborn BRGS mice were intrahepatic transferred with 1-3×10$^5$ CD117$^+$ ILC or CD34$^+$ HSC freshly isolated by FACS from PB of healthy individuals. The progeny of these populations were analyzed 4 weeks post-injection. (B) FACS analysis for lymphocytes and myeloid surface markers gated on viable human CD45$^+$ cells from bone marrow and gut of BRGS mice transferred with CD117$^+$ ILC or control CD34$^+$ HSC. (C) FACS analysis of different ILC subsets by surface NKp44 and CD117 expression, intracellular EOMES and intracellular cytokines (IFN-γ, IL-13, IL-22 and IL-17A) production in lung, gut, liver and spleen of BRGS mice transferred with CD117$^+$ ILC. Representative data of at least 4 mice in each group from 3 independent experiments.

Example 4: Circulating CD117$^+$ ILCP have Multi-ILC Potential In Vivo in Humanized Mice The in vivo potential of PB CD117$^+$ ILCP was next assessed. Previous studies have demonstrated the capacity of severely immunodeficient mouse strains engrafted with human CD34$^+$ hematopoietic stem cell (HSC) progenitors to generate human lymphoid (B, T, NK) and myeloid (DC, macrophage, neutrophils) cell subsets (reviewed in (Shultz et al., 2012)). BALB/c Rag2$^{-/-}$Il2rg$^{-/-}$Sirpa$^{NOD}$ (BRGS) mice that are permissive for robust multi-lineage human hematopoietic cell engraftment were used (Legrand et al., 2011). Human PB CD34$^+$ HSC and CD117$^+$ ILCP from same donors were adoptively transferred to newborn BRGS mice; cytokine supplementation (IL-2, IL-7, IL-1$\beta$, IL-23) was provided and mice were analyzed 4 weeks later (FIG. 4A). BRGS mice engrafted with human CD34$^+$ HSC developed CD19$^+$ B cells and CD14/CD33$^+$ myeloid cells in the bone marrow, while CD3/CD5$^+$ T cells and Lin$^-$ CD7$^+$ NK/ILC were detected in the gut (FIG. 4B). In contrast, BRGS mice receiving PB CD117$^+$ ILCP developed Lin$^-$CD7$^+$ cells but no myeloid cells, B cells or T cells. Human CD45$^+$ progeny from transferred CD117$^+$ ILCP were detected in multiple organs, including the spleen, lung, gut and liver (FIG. 4C). At each of these tissue sites, EOMES$^+$ NK cells as well as diverse CD127$^+$ ILC subsets could be identified that produced IFN-$\gamma$, IL-13, IL-17A and/or IL-22 ex vivo upon stimulation (FIG. 4C). These results demonstrate that PB CD117$^+$ ILCP have the potential to generate all known ILC subsets and NK cells in vivo. Since PB CD117$^+$ ILCP lack myeloid, B and T cell potential, it was concluded that these cells comprise committed ILC progenitors.

Example 5: Human CD117$^+$ ILCP Develop from CD34$^+$ HSC In Vivo

The developmental relationship between CD34$^+$ HSC and CD117$^+$ ILCP was next interrogated. Immunodeficient neonatal BRGS mice were engrafted with purified CD34$^+$ HSC and were sacrificed 8-9 weeks later (FIG. 5A). Human CD45$^+$ cells were analyzed in bone marrow, lung, liver and spleen. As expected (Legrand et al., 2011), these different tissue sites harbored human CD45$^+$ cells, including a variety of lineage$^+$ T, B and myeloid cells (FIG. 5B, data not shown). Moreover, within the subset of Lin$^-$CD7$^+$ cells, a clearly defined subpopulation of CD127$^+$CD117$^+$ cells could be discerned in multiple tissues that lacked T-BET and EOMES expression (FIG. 5B). These included CD127$^+$ CD117$^+$ cells that expressed low levels of GATA-3 and ROR$\gamma$t and were NKp44$^-$ (FIG. 5D) and therefore resembled PB CD117$^+$ ILCP. Ex vivo stimulation failed to elicit cytokine production from CD127$^+$CD117$^+$ cells (FIG. 5E). These cells were sorted and bulk cultured in the presence of IL-2, IL-7, IL-1$\beta$ and IL-23. Expanded cells contained subsets able to produce IFN-$\gamma$, IL-13, IL-17A and IL-22 (FIG. 5E) thereby confirming the presence of human ILCP. These results demonstrate that CD34$^+$ HSC can give rise to CD117$^+$ ILCP in vivo.

Example 6: Human CD117$^+$ ILCP are Present in Fetal Liver, Cord Blood and Adult Lung The stage of development when human CD117$^+$ ILCP arise was next assessed. Human ILC subsets in fetal liver (FL) were first studied as this organ has been shown to harbor several immature hematopoietic precursor populations (Rollini et al., 2007) and is proposed as a sight for the development of lymphoid tissue inducer cells in the mouse (Cherrier et al., 2012). Lin CD127$^+$ ILC within FL contain a predominant CD117$^+$ subset. Interestingly, these cells express ROR$\gamma$t at levels exceeding their peripheral blood counterparts (FIG. 1C) and moreover express CCR6, Neuropilin-1 (NRP-1) but not NKp44. Despite these differences, FL CD117$^+$ ILC did not produce significant amounts of IL-17A or IL-22 after stimulation suggesting that they were not fully mature ILC3. Nevertheless, when FL CD117$^+$ ILC were expanded in vitro, IL-17A-producing ILC3 were abundantly generated. Moreover, IL17A$^+$ ILC3 developed on stromal cells lacking DL4 suggesting that additional Notch engagement was not necessary for this process (FIG. 6A). Interestingly, bulk cultures of FL CD117$^+$ ILC also contain detectable IL-13- and IFN-$\gamma$-producing cells, although at lower frequency. Clonal analysis revealed that FL CD117$^+$ ILC harbor, as expected, a high proportion of ILC3 committed progenitors. Still, a substantial fraction of this population includes multi-potent ILCP (FIG. 6B, C) that are more clearly revealed in the presence of Notch ligands. These results demonstrate that the human FL harbors CD34$^-$CD127$^+$CD117$^+$ multi-potent ILCP that can generate all known ILC subsets. The enrichment of ILC3-committed progenitors in this tissue site suggests that environmental signals may direct the further specification of multi-potent ILCP towards an ILC3 fate during this period.

CD117$^+$ ILC from human cord blood (CB) were next characterized. Like their PB counterparts, CB CD117$^+$ ILC lacked NKp44 expression as well as that of CCR6 and NRP-1 and were CD45RA$^+$. Moreover, CB CD117$^+$ ILC failed to express RORγt and T-BET but were GATA-3$^{lo}$, thus resembling PB ILCP. Like PB CD117$^+$ ILC, CB CD117$^+$ ILC did not produce cytokines (IFN-γ, IL-13, IL-17A or IL-22) ex vivo after stimulation. However, bulk culture of CB CD117$^+$ ILC in IL-2, IL-7, IL-1β and IL-23 generated diverse cytokine-producing ILC subsets that included IFN-γ ILC1, IL-13$^+$ ILC2 and IL-17A$^+$ or IL-22$^+$ ILC3 (FIG. 6D). No T, B or myeloid cells were detected in cultures of CB CD117$^+$ ILC (data not shown). Further clonal analysis revealed that CB CD117$^+$ ILC harbored a diverse mix of uni-potent and multi-potent ILCP (FIGS. 6E and 6F). Unlike FL CD117$^+$ ILC, CB CD117$^+$ ILC were not biased towards ILC3-committed progenitors, but more closely resembled PB CD117$^+$ ILCP. As for ILCP from PB or FL, Notch stimulation resulted in an enhanced frequency of multi-potent ILCP (especially those having the potential for IL-17A$^+$ and IL-22$^+$ ILC3) and reduced the frequency of cytokine ILC clones, suggesting that this pathway facilitated directed development of specific ILC subsets.

The phenotype and potential of CD117$^+$ ILC from adult lung tissue was also examined. Lung CD117$^+$ ILC harbored discreet populations of NKp44$^+$ and RORγt$^+$ ILC but were largely CD45A$^-$. Bulk cultures of lung CD117$^+$ ILC generated diverse cytokine-producing ILC subsets and EOMES$^+$ NK cells (FIG. 6G); further analysis using clonal assays defined the NKp44$^-$ fraction of lung CD117$^+$ ILC as a mixture of uni-potent and multi-potent ILCP (FIGS. 6H and 6I). These results demonstrate that a variety of ILCP, including multi-potent progenitors, are present in human mucosal tissues.

Example 7: ILC Precursors Reside within Secondary Lymphoid Tissues

Human secondary lymphoid tissues (lymph nodes, tonsils) harbor diverse ILC subsets and their precursors (Bernink et al., 2013; Cella et al., 2009; Fehniger et al., 2003; Mjösberg et al., 2011; Renoux et al., 2015; Montaldo et al., 2015; Scoville et al., 2016). It was therefore of interest to further characterize tonsillar CD117$^+$ ILCP and to assess their cell fate potential. CD117$^+$ ILC from pediatric tonsils harbor a predominant NKp44$^+$ ILC3 subset that can be stimulated to produce IL-17A and IL-22 (Hoorweg et al., 2012). This population also appears to have extensive functional plasticity as stimulation (using IL-1β, IL-12, IL-23) can modify cytokine outputs of these cells (Bernink et al., 2015; Bernink et al., 2013; Cella et al., 2010). Within tonsillar CD117$^+$ ILC, it was found that NKp44$^-$ cells were CD45RA$^+$ and NRP-1$^-$, while NKp44$^+$ cells were CD45RA$^-$ and NRP-1$^+$. These suggest that NKp44$^+$ ILC3 are more mature and differentiate from NKp44$^-$ cells (Bernink et al., 2015). However, cytokine production profiles were different in bulk cultures from tonsillar NKp44$^-$ versus NKp44$^+$ CD117$^+$ ILC (FIGS. 6J and 6M). In particular, IFN-γ$^+$ cells and IL-13$^+$ cells were more obvious in cultures derived from NKp44$^-$ cells, especially on OP9 stroma (FIG. 6J).

In order to better understand the relationship between NKp44$^+$ and NKp44$^+$CD117$^+$ ILC, clones from both subsets were generated and their cytokine-production potential analyzed. Striking differences were observed. Clones derived from NKp44$^+$ CD117$^+$ ILC were highly enriched ILC3 producing IL-17A and/or IL-22 (FIGS. 6N and 6O). A fraction of clones co-expressed IFN-γ (14%) that likely represent 'plastic' ILC3 that may up-regulate T-BET as previously shown (Bernink et al., 2015). In contrast, clones derived from NKp44$^-$ CD117$^+$ ILC were quite heterogeneous with cells producing not only IL-22 and/or IL-17A but also abundant single IFN-γ$^+$ clones as well as single IL-13$^+$ clones (FIGS. 6K and 6L) that were not detected from NKp44$^+$ CD117$^+$ ILC (FIGS. 6N and 6O). The fact that IFN-γ$^+$ ILC1 clones were observed was unexpected given the previous reports that tonsillar CD127$^+$ ILC1 differentiate into IL-22 producing ILC3 in the presence of IL-2, IL-23 and IL-1β (Bernink et al., 2015). Lastly, multi-potent ILCP giving rise to three ILC subsets were only found in NKp44$^-$ CD117$^+$ ILC. Taken together, these results suggest that tonsillar CD117$^+$ ILC are quite heterogeneous comprising NKp44$^-$ ILCP as well as NKp44$^+$ ILC3. Furthermore, the inventors' use of clonal assays clearly allows the definition of ILCP repertoires that is not visualized at the bulk culture level.

Example 8: RORC-Deficient Patients Harbor ILCP but Fail to Generate IL-17A$^+$ ILC3

Figure 7:
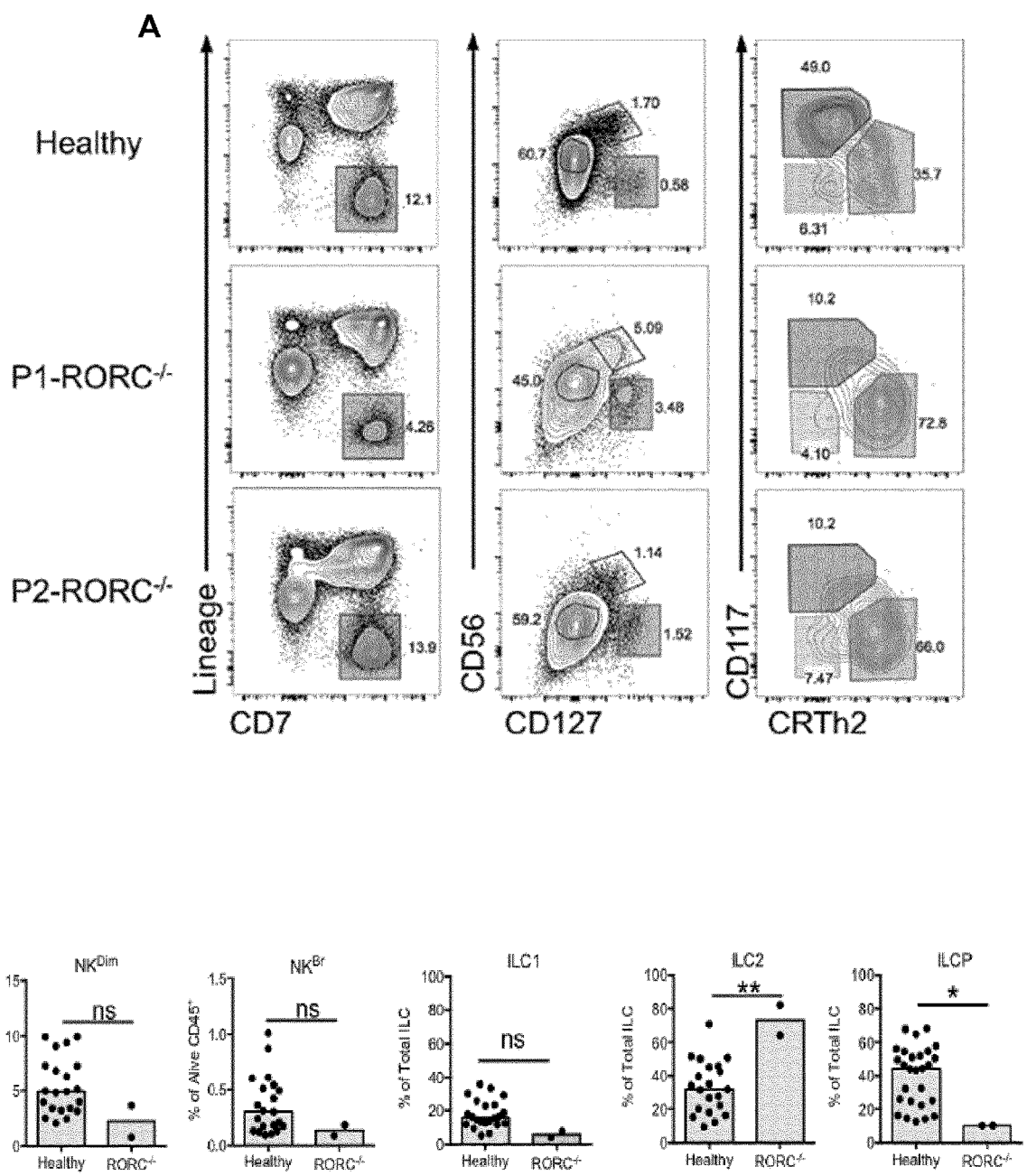
FIG. 7 A-C depict the developmental potential of ILCP from RORC$^{-/-}$ patients (A) FACS analysis of peripheral blood ILC subsets from healthy and RORC$^{-/-}$ patients sample. (B) Percentage of NK$^{Dim}$ and NK$^{Br}$ from viable CD45$^+$ cells, ILC, ILC2 and ILCP from total ILC of PB of healthy and RORC$^{-/-}$ patients. Result from 22 healthy donors and 2 RORC$^{-/-}$ patients. ns, P>0.05; *, P<0.05; **, P<0.01 using paired Student's t test (Median) (C) ILCP from healthy donor or RORC$^{-/-}$ patients were FACS sorted and cultured on OP9-DL4 with IL-2,-7, -1β and -23 for 8 days. Surface phenotypes, intracellular EOMES expression and cytokines production profiles were analyzed after 3 h stimulation with PMA/iono.

A committed ILCP in human secondary lymphoid tissue with a CD34$^+$CD45RA$^+$CD117$^+$ phenotype was shown to highly express the TF RORC (Scoville et al., 2016). As CD117$^+$ ILCP are developmentally downstream from CD34$^+$ HSC (FIG. 5), it is possible that the previously described CD34$^+$CD45RA$^+$CD117$^+$ ILCP subset is an intermediate in this pathway. In order to address whether RORC was required for generation of human CD117$^+$ ILCP RORC-deficient patients were studied. RORC deficiency in humans is associated with mucocutaneous candidiasis and previous studies demonstrated that this TF is essential for differentiation of Th17 cells that protect against fungal pathogens (Okada et al., 2015). ILC subsets from peripheral blood cells from 2 patients with RORC deficiency were studied (FIG. 7A). Lin$^-$CD7$^+$ cells contained a predominant population of CD56$^+$ NK cells (both CD56$^{bright}$ and CD56$^{dim}$) in both controls and RORC-deficient patients and a discreet subpopulation of CD127$^+$ ILCs was also clearly detected. As previously described (Okada et al., 2015), a reduction in the frequency of CD117-expressing ILC was noted in patients with RORC deficiency, although this population was still clearly present (FIGS. 7A and 7B). In contrast, ILC1 were present and the percentage of ILC2 from total ILC was significantly increased in the absence of RORC (FIG. 7B). Sorted CD117$^+$ ILC from control and RORC-deficient patients were bulk cultured as described above. Robust growth of Lin$^-$CD7$^+$ cells was observed with no significant difference between WT and RORC-deficient cells. Diverse cytokine producing cells were identified in these cultures, including those producing IFN-γ, IL-13 or IL-22, however, no IL-17A-producing cells were present (FIG. 7C). Development of EOMES$^+$IFN-γ$^+$ NK cells was not affected by the absence of RORC. These results demonstrate that RORC is not required for the development of NK cells, ILC1, ILC2 or IL-22$^+$ ILC3 but is essential for the generation of IL-17A$^+$ ILC3 from ILCP in humans.

Example 9: Analysis of ILCP Markers in Blood

While CD127 and CD117 are expressed by ILCP, they are not specific. To gain insights into minimal essential markers, combinations of markers that could be used to highly enrich for ILCP were analysed. Therefore, percentages of different cell types was determined by FACS using different markers to isolate cells from adult peripheral blood. The results present analysis of the enrichment for human ILCP in peripheral blood using multi-parametric FACS analysis. Using the different gating scheme, one can estimate the enrichment of ILCP as well as other cell types (T cells, NK cells, ILC2) that may be present. The results are presented in FIG. 8A-F and FIG. 9A-G.

Sorting using the markers CD127+CD117+ cells generated about 20% ILCP and 60-80% T cells (FIGS. 8A and 9A). Including CD7, excluding CRTh2 or a combination of both were not sufficient to enrich ILCP within CD127+CD117+ cells since contaminating T cells predominated (FIG. 8A-D: FIG. 9A-D). Excluding Lineage cells (including CD3) strongly enriched ILCP in CD127+CD117+ cells (FIG. 8E-F; FIG. 9E-G). Exclusion of CRTh2 ILC2 in Lin−CD127+CD117+ cells provided further ILCP enrichment, generating at least 75% of ILCP (FIG. 9E). CD7 was not required for this effect (FIGS. 8E and 9F). Excluding CD94 allowed isolation of pure ILCP from Lin−CD127+CD117+CRTh2− cells (FIGS. 8F and 9G). Accordingly, sorting using the markers CD127+CD117+CD7+CRTh2−Lin− generated approximately 90% ILCP (FIGS. 8E and 9F) and sorting using the markers CD127+CD117+CRTh2−Lin−CD94− generated approximately 100% ILCP (FIGS. 8F and 9G).

Example 10: Additional ILCP Markers

Human ILCP (defined as Lin−CD127+CD117+CRTh2−) were additionally screened for expression of additional cell surface markers that could be useful surrogates for isolating these cells. Variable CD62L and CD26 expression were identified on human ILCP with most cells being CD62L+ and a large proportion of cells expressing CD26 (FIG. 10).

Clonal analysis demonstrated that all of these subsets harbored multi-potent ILCP (Table 1).

TABLE 1

Clonal analysis of CD62L and CD26 human ILCP subsets.

|  | ILCP CD62L+CD26− | ILCP CD62L+CD26+ | ILCP CD62L−CD26− | ILCP CD62L−CD26+ |
| --- | --- | --- | --- | --- |
| No cytokine | 21; 33% | 2; 3% | 13; 42% | 10; 16% |
| Multipotent | 7; 11% | 25; 40% | 3; 10% | 20; 32% |
| ILC1 | 2; 3% | 3; 5% | 2; 6% | 3; 5% |
| ILC2 | 29; 46% | 25; 41% | 11; 36% | 28; 44% |
| ILC3 | 0; 0% | 0; 0% | 0; 0% | 0; 0% |
| NK | 4; 7% | 7; 11% | 2; 6% | 2; 3% |

Indicated human ILCP subsets were sorted as single cells and cultured on OP9 stroma supplemented with human IL-1b, IL-2, IL-7 and IL-23. Clones were then analyzed for cytokine production (IFNg, IL-13, IL-17A, IL-22) after 3 hr stimulation with PMA/ionomycin. Frequencies of uni-potent and multipotent ILCP are indicated. Putative ILCP are identified as 'No cytokine'.

These results identify additional 'optional' markers (CD62L, CD26) that can be used to isolate subsets of human ILCP.

Human ILCP expansion: Analysis of human ILCP clones (using OP9 stromal cells and combinations of IL-2, IL-7, IL-1β and IL-23 identified cells that failed to express any tested cytokines (IFN-g, IL-13, IL-17A, IL-22). These ILCP 'clones' had expanded between 100- and 1000-fold in number (FIG. 11). These cells were phenotypes and found to express CD117, CD45RA and CD26 but were CD62L− (FIG. 12). Recloning experiments showed that these cells continued to have multi-potency for all ILC subsets. It was concluded that human ILCP can be expanded using combinations of stromal cells and cytokines and retain functional properties.

REFERENCES

Artis, D., and Spits, H. (2015). The biology of innate lymphoid cells. Nature 517, 293-301.

Baum, C. M., Weissman, I. L., Tsukamoto, A. S., Buckle, A. M., and Peault, B. (1992). Isolation of a candidate human hematopoietic stem-cell population. Proc Natl Acad Sci USA 89, 2804-2808.

Bernink, J. H., Krabbendam, L., Germar, K., de Jong, E., Gronke, K., Kofoed-Nielsen, M., Munneke, J. M., Hazenberg, M. D., Villaudy, J., Buskens, C. J., et al. (2015). Interleukin-12 and -23 Control Plasticity of CD127(+) Group 1 and Group 3 Innate Lymphoid Cells in the Intestinal Lamina Propria. Immunity 43, 146-160.

Bernink, J. H., Peters, C. P., Munneke, M., te Velde, A. A., Meijer, S. L., Weijer, K., Hreggvidsdottir, H. S., Heinsbroek, S. E., Legrand, N., Buskens, C. J., et al. (2013). Human type 1 innate lymphoid cells accumulate in inflamed mucosal tissues. Nat Immunol 14, 221-229.

Cella, M., Fuchs, A., Vermi, W., Facchetti, F., Otero, K., Lennerz, J. K., Doherty, J. M., Mills, J. C., and Colonna, M. (2009). A human natural killer cell subset provides an innate source of IL-22 for mucosal immunity. Nature 457, 722-725.

Cella, M., Otero, K., and Colonna, M. (2010). Expansion of human NK-22 cells with IL-7, IL-2, and IL-1beta reveals intrinsic functional plasticity. Proc Natl Acad Sci USA 107, 10961-10966.

Chea, S., Perchet, T., Petit, M., Verrier, T., Guy-Grand, D., Banchi, E. G., Vosshenrich, C. A., Di Santo, J. P., Cumano, A., and Golub, R. (2016a). Notch signaling in group 3 innate lymphoid cells modulates their plasticity. Sci Signal 9, ra45.

Chea, S., Schmutz, S., Berthault, C., Perchet, T., Petit, M., Burlen-Defranoux, O., Goldrath, A. W., Rodewald, H. R., Cumano, A., and Golub, R. (2016b). Single-Cell Gene Expression Analyses Reveal Heterogeneous Responsiveness of Fetal Innate Lymphoid Progenitors to Notch Signaling. Cell Rep 14, 1500-1516.

Cherrier, M., Sawa, S., and Eberl, G. (2012). Notch, Id2, and RORγt sequentially orchestrate the fetal development of lymphoid tissue inducer cells. J Exp Med 209, 729-740.

Constantinides, M. G., McDonald, B. D., Verhoef, P. A., and Bendelac, A. (2014). A committed precursor to innate lymphoid cells. Nature 508, 397-401.

Cupedo, T., Crellin, N. K., Papazian, N., Rombouts, E. J., Weijer, K., Grogan, J. L., Fibbe, W. E., Cornelissen, J. J., and Spits, H. (2009). Human fetal lymphoid tissue-inducer cells are interleukin 17-producing precursors to RORC+ CD127+ natural killer-like cells. Nat Immunol 10, 66-74.

Dallas, M. H., Varnum-Finney, B., Delaney, C., Kato, K., and Bernstein, I. D. (2005). Density of the Notch ligand Delta1 determines generation of B and T cell precursors from hematopoietic stem cells. J Exp Med 201, 1361-1366.

Diefenbach, A., Colonna, M., and Koyasu, S. (2014). Development, differentiation, and diversity of innate lymphoid cells. Immunity 41, 354-365.

Eberl, G., Colonna, M., Di Santo, J. P., and McKenzie, A. N. (2015). Innate lymphoid cells. Innate lymphoid cells: a new paradigm in immunology. Science 348, aaa6566.

Fuchs, A., Vermi, W., Lee, J. S., Lonardi, S., Gilfillan, S., Newberry, R. D., Cella, M., and Colonna, M. (2013). Intraepithelial type 1 innate lymphoid cells are a unique subset of IL-12- and IL-15-responsive IFN-γ-producing cells. Immunity 38, 769-781.

Gasteiger, G., Fan, X., Dikiy, S., Lee, S. Y., and Rudensky, A. Y. (2015). Tissue residency of innate lymphoid cells in lymphoid and nonlymphoid organs. Science 350, 981-985.

Hazenberg, M. D., and Spits, H. (2014). Human innate lymphoid cells. Blood 124, 700-709.

Hoorweg, K., Peters, C. P., Cornelissen, F., Aparicio-Domingo, P., Papazian, N., Kazemier, G., Mjösberg, J. M., Spits, H., and Cupedo, T. (2012). Functional Differences between Human NKp44(−) and NKp44(+) RORC(+) Innate Lymphoid Cells. Front Immunol 3, 72.

Ikuta, K., and Weissman, I. L. (1992). Evidence that hematopoietic stem cells express mouse c-kit but do not depend on steel factor for their generation. Proc Natl Acad Sci USA 89, 1502-1506.

Juelke, K., and Romagnani, C. (2016). Differentiation of human innate lymphoid cells (ILCs). Curr Opin Immunol 38, 75-85.

Kikushige, Y., Yoshimoto, G., Miyamoto, T., Iino, T., Mori, Y., Iwasaki, H., Niiro, H., Takenaka, K., Nagafuji, K., Harada, M., et al. (2008). Human Flt3 is expressed at the hematopoietic stem cell and the granulocyte/macrophage progenitor stages to maintain cell survival. J Immunol 180, 7358-7367.

Kim, B. S., and Artis, D. (2015). Group 2 innate lymphoid cells in health and disease. Cold Spring Harb Perspect Biol 7.

Klose, C. S., Flach, M., Möhle, L., Rogell, L., Hoyler, T., Ebert, K., Fabiunke, C., Pfeifer, D., Sexl, V., Fonseca-Pereira, D., et al. (2014). Differentiation of type 1 ILCs from a common progenitor to all helper-like innate lymphoid cell lineages. Cell 157, 340-356.

Koues, O. I., Collins, P. L., Cella, M., Robinette, M. L., Porter, S. I., Pyfrom, S. C., Payton, J. E., Colonna, M., and Oltz, E. M. (2016). Distinct Gene Regulatory Pathways for Human Innate versus Adaptive Lymphoid Cells. Cell 165, 1134-1146.

Langmead, B., and Salzberg, S. L. (2012). Fast gapped-read alignment with Bowtie 2. Nat Methods 9, 357-359.

Legrand, N., Huntington, N. D., Nagasawa, M., Bakker, A. Q., Schotte, R., Strick-Marchand, H., de Geus, S. J., Pouw, S. M., Böhne, M., Voordouw, A., et al. (2011). Functional CD47/signal regulatory protein alpha (SIRP (alpha)) interaction is required for optimal human T- and natural killer- (NK) cell homeostasis in vivo. Proc Natl Acad Sci USA 108, 13224-13229.

Lim, A. I., Menegatti, S., Bustamante, J., Le Bourhis, L., Allez, M., Rogge, L., Casanova, J. L., Yssel, H., and Di Santo, J. P. (2016). IL-12 drives functional plasticity of human group 2 innate lymphoid cells. J Exp Med 213, 569-583.

Luci, C., Reynders, A., Ivanov, I. I., Cognet, C., Chiche, L., Chasson, L., Hardwigsen, J., Anguiano, E., Banchereau, J., Chaussabel, D., et al. (2009). Influence of the transcription factor RORgammat on the development of NKp46+ cell populations in gut and skin. Nat Immunol 10, 75-82.

Mjösberg, J. M., Trifari, S., Crellin, N. K., Peters, C. P., van Drunen, C. M., Piet, B., Fokkens, W. J., Cupedo, T., and Spits, H. (2011). Human IL-25- and IL-33-responsive type 2 innate lymphoid cells are defined by expression of CRTH2 and CD161. Nat Immunol 12, 1055-1062.

Mohtashami, M., Shah, D. K., Nakase, H., Kianizad, K., Petrie, H. T., and Zúñiga-Pflücker, J. C. (2010). Direct comparison of Dll1- and Dll4-mediated Notch activation levels shows differential lymphomyeloid lineage commitment outcomes. J Immunol 185, 867-876.

Montaldo, E., Juelke, K., and Romagnani, C. (2015). Group 3 innate lymphoid cells (ILC3s): Origin, differentiation, and plasticity in humans and mice. Eur J Immunol 45, 2171-2182.

Montaldo, E., Teixeira-Alves, L. G., Glatzer, T., Durek, P., Stervbo, U., Hamann, W., Babic, M., Paclik, D., Stölzel, K., Gröne, J., et al. (2014). Human RORγt(+)CD34(+) cells are lineage-specified progenitors of group 3 RORγt (+) innate lymphoid cells. Immunity 41, 988-1000.

Munneke, J. M., Björklund, A. T., Mjösberg, J. M., Garming-Legert, K., Bernink, J. H., Blom, B., Huisman, C., van Oers, M. H., Spits, H., Malmberg, K. J., et al. (2014). Activated innate lymphoid cells are associated with a reduced susceptibility to graft-versus-host disease. Blood 124, 812-821.

Okada, S., Markle, J. G., Deenick, E. K., Mele, F., Averbuch, D., Lagos, M., Alzahrani, M., Al-Muhsen, S., Halwani, R., Ma, C. S., et al. (2015). IMMUNODEFICIENCIES. Impairment of immunity to Candida and Mycobacterium in humans with bi-allelic RORC mutations. Science 349, 606-613.

Rollini, P., Faes-Van't Hull, E., Kaiser, S., Kapp, U., and Leyvraz, S. (2007). Phenotypic and functional analysis of human fetal liver hematopoietic stem cells in culture. Stem Cells Dev 16, 281-296.

Sawa, S., Cherrier, M., Lochner, M., Satoh-Takayama, N., Fehling, H. J., Langa, F., Di Santo, J. P., and Eberl, G. (2010). Lineage relationship analysis of RORgammat+ innate lymphoid cells. Science 330, 665-669.

Schmidl, C., Rendeiro, A. F., Sheffield, N. C., and Bock, C. (2015). ChIPmentation: fast, robust, low-input ChIP-seq for histones and transcription factors. Nat Methods 12, 963-965.

Scoville, S. D., Mundy-Bosse, B. L., Zhang, M. H., Chen, L., Zhang, X., Keller, K. A., Hughes, T., Cheng, S., Bergin, S. M., Mao, H. C., et al. (2016). A Progenitor Cell Expressing Transcription Factor RORγt Generates All Human Innate Lymphoid Cell Subsets. Immunity 44, 1140-1150.

Seehus, C. R., Aliahmad, P., de la Torre, B., Iliev, I. D., Spurka, L., Funari, V. A., and Kaye, J. (2015). The development of innate lymphoid cells requires TOX-dependent generation of a common innate lymphoid cell progenitor. Nat Immunol 16, 599-608.

Serafini, N., Vosshenrich, C. A., and Di Santo, J. P. (2015). Transcriptional regulation of innate lymphoid cell fate. Nat Rev Immunol 15, 415-428.

Shih, H. Y., Sciume, G., Mikami, Y., Guo, L., Sun, H. W., Brooks, S. R., Urban, J. F., Davis, F. P., Kanno, Y., and O'Shea, J. J. (2016). Developmental Acquisition of Regulomes Underlies Innate Lymphoid Cell Functionality. Cell 165, 1120-1133.

Shultz, L. D., Brehm, M. A., Garcia-Martinez, J. V., and Greiner, D. L. (2012). Humanized mice for immune system investigation: progress, promise and challenges. Nat Rev Immunol 12, 786-798.

Spits, H., Artis, D., Colonna, M., Diefenbach, A., Di Santo, J. P., Eberl, G., Koyasu, S., Locksley, R. M., McKenzie, A. N., Mebius, R. E., et al. (2013). Innate lymphoid cells—a proposal for uniform nomenclature. Nat Rev Immunol 13, 145-149.

Vély, F., Barlogis, V., Vallentin, B., Neven, B., Piperoglou, C., Ebbo, M., Perchet, T., Petit, M., Yessaad, N., Touzot, F., et al. (2016). Evidence of innate lymphoid cell redundancy in humans. Nat Immunol 17, 1291-1299.

Yagi, R., Zhong, C., Northrup, D. L., Yu, F., Bouladoux, N., Spencer, S., Hu, G., Barron, L., Sharma, S., Nakayama, T., et al. (2014). The transcription factor GATA3 is critical for the development of all IL-7Rα-expressing innate lymphoid cells. Immunity 40, 378-388.

Yang, Q., Li, F., Harly, C., Xing, S., Ye, L., Xia, X., Wang, H., Wang, X., Yu, S., Zhou, X., et al. (2015). TCF-1 upregulation identifies early innate lymphoid progenitors in the bone marrow. Nat Immunol 16, 1044-1050.

Zook, E. C., Ramirez, K., Guo, X., van der Voort, G., Sigvardsson, M., Svensson, E. C., Fu, Y. X., and Kee, B. L. (2016). The ETS1 transcription factor is required for the development and cytokine-induced expansion of ILC2. J Exp Med 213, 687-696.

The invention claimed is:

1. A method for making a purified population of innate lymphoid cell precursors (ILCPs) comprising:
providing a human peripheral blood cell sample, and
selecting for ILCPs in the peripheral blood cell sample that have the phenotype
CD127+CD117+CD3−CRTh2−CD7+CD94−NKp44−CD26+,
CD127+CD117+CD3−CRTh2−CD7+CD94−NKp44−CD62L+, or
CD127+CD117+CD3−CRTh2−CD7+CD94−NKp44−CD26+CD62L+ to provide a selected population of cells, wherein at least 75% of the cells in the selected population have the phenotype
CD127+CD117+CD3−CRTh2−CD7+CD94−NKp44−CD26+,
CD127+CD117+CD3−CRTh2−CD7+CD94−NKp44−CD62L+, or
CD127+CD117+CD3−CRTh2−CD7+CD94−NKp44−CD26+CD62L+.

2. The method of claim 1, further comprising subjecting the cell population to an external stimulus after the selection step, and detecting an increase in a cell type selected from ILC1, ILC2, ILC3, and NK cells.

3. The method of claim 2, wherein at least 90% of the cells in the population have the phenotype
CD127+CD117+CD3−CRTh2−CD7+CD94−NKp44−CD26+,
CD127+CD117+CD3−CRTh2−CD7+CD94−NKp44−CD62L+, or
CD127+CD117+CD3−CRTh2−CD7+CD94−NKp44−CD26+CD62L+.

4. The method of claim 2, wherein subjecting the cell population to an external stimulus is performed in vivo.

5. The method of claim 1, wherein the ILCPs are cultured in a culture medium that comprises IL-1ß and IL-2.

6. The method of claim 2, wherein the external stimulus comprises culturing the cell population in a culture medium comprising IL-1ß IL-2 and IL-7.

7. The method of claim 1, wherein the cells in the selected population have the phenotype CD127+CD117+CD3−CRTh2−CD7+CD94−NKp44−CD26+.

8. The method of claim 1, wherein the cells in the selected population have the phenotype CD127+CD117+CD3−CRTh2−CD7+CD94−NKp44−CD62 L+.

9. The method of claim 1, wherein the cells in the selected population have the phenotype CD127+CD117+CD3−CRTh2−CD7+CD94−NKp44−CD26+CD62L+.

\* \* \* \* \*